US012759975B2

(12) United States Patent
Li et al.

(10) Patent No.: US 12,759,975 B2
(45) Date of Patent: Oct. 13, 2026

(54) METHOD FOR PREPARING INTERMEDIATE FOR USE IN SYNTHESIS OF FLORFENICOL AND COMPOUNDS PREPARED THEREBY

(71) Applicant: HEADING (NANJING) PHARMTECHNOLOGIES CO., LTD., Nanjing (CN)

(72) Inventors: Wensen Li, Nanjing (CN); Wenqi Zhang, Nanjing (CN)

(73) Assignee: HEADING(NANJING) PHARM TECHNOLOGIES CO., LTD., Nanjing (CN)

( * ) Notice: Subject to any disclaimer, the term of this patent is extended or adjusted under 35 U.S.C. 154(b) by 974 days.

(21) Appl. No.: 17/906,475

(22) PCT Filed: Aug. 6, 2020

(86) PCT No.: PCT/CN2020/107352
§ 371 (c)(1),
(2) Date: Sep. 16, 2022

(87) PCT Pub. No.: WO2021/184649
PCT Pub. Date: Sep. 23, 2021

(65) Prior Publication Data

US 2023/0183175 A1 Jun. 15, 2023

(30) Foreign Application Priority Data

Mar. 16, 2020 (CN) ........................ 202010184089.7

(51) Int. Cl.
*C07C 315/02* (2006.01)
*B01J 31/28* (2006.01)

(52) U.S. Cl.
CPC ............ *C07C 315/02* (2013.01); *B01J 31/28* (2013.01)

(58) Field of Classification Search
None
See application file for complete search history.

(56) References Cited

U.S. PATENT DOCUMENTS

| | | | |
|---|---|---|---|
| 3,927,054 | A | 12/1975 | Tobiki et al. |
| 10,597,353 | B2 | 3/2020 | Barreca et al. |
| 2008/0319200 | A1 | 12/2008 | Towson |

OTHER PUBLICATIONS

Kisanga et al. (Tetrahedron Letters, 2001, 42, 6263, pub date Jul. 13, 2001) (Year: 2001).*
International Search Report PCT/CN2020/107352, Mailed Nov. 24, 2020.

* cited by examiner

*Primary Examiner* — Renee Claytor
*Assistant Examiner* — Jennifer C Sawyer
(74) *Attorney, Agent, or Firm* — Yuhao Liang

(57) ABSTRACT

The present invention provides a method for preparing an intermediate of florfenicol, comprising: reacting p-methylthiobenzaldehyde with isocyanoacetate under catalysis of a chiral catalyst. In the reaction, the chiral product is oxidized to form a methylsulfone-substituted product which is subsequently deformylized to obtain the intermediate. In the method of the present invention, the chiral center of the intermediate is directly generated in the first step of reaction, and the yield of the first step reaches 75%-80%, which is significantly higher than the conventional chiral resolution methods (about 40% yield), and the product has high chiral purity. The method of the present invention does not use anhydrous copper sulfate that pollutes the environment, which reduces the environmental pressure. The compound of p-methylthiobenzaldehyde and the compound of isocyanoacetate are used to react to form a chiral intermediate, which has higher material availability and efficiency than linear synthesis methods.

14 Claims, 23 Drawing Sheets

| No. | RT | Area | Conc 1 |
|---|---|---|---|
| 1 | 2.69 | 38307 | 1.394 |
| 2 | 4.21 | 2710414 | 98.606 |
| | | 2748721 | 100.000 |

Operator : Sequence row : 1
Instrument : Intrument 1 Position : Vial 14
Date of injection : 2018/8/10 15:13:35 Injection repetition : 1
Injection volume : 5.000 µl
Acquisition method : D: \CHEM32\1\DATA\HDP107\HDP107 2018-08-10 15-12-05\HDP107-G-CHIRAL.M
Last revised : 2018/8/9 20:33:04
Last revised : 2018/8/6 9:57:51
(Revised after retrieval)
Additioinal Info.: Peaks have been manually integrated

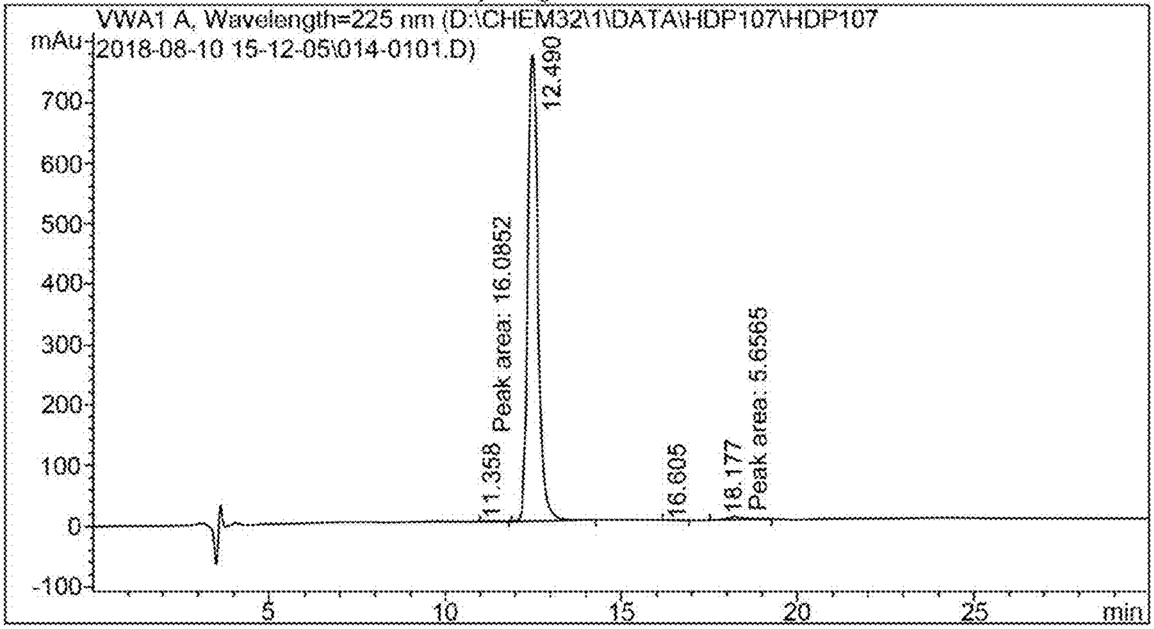

Report for area percentage

Sequence : Signal
Produce factor : 1.0000
Dilution factor : 1.0000
Product factor and dilution factor for internal standard Signal 1: VWD1 A, Wavelength=225 nm

| Peak # | RT. [min] | Type | Peak width [min] | Peak Area [mAu*s] | Peak Height [mAu] | Peak area % |
|---|---|---|---|---|---|---|
| 1 | 11.358 | MM | 0.3755 | 16.08519 | 7.13889e-1 | 0.1056 |
| 2 | 12.490 | BB | 0.3026 | 1.52430e4 | 764.45221 | 98.7400 |
| 3 | 16.605 | MM | 0.2901 | 5.65650 | 2.36611e-1 | 0.0371 |
| 4 | 18.177 | BB | 0.4771 | 170.22444 | 5.30892 | 1.1173 |
| Total: | | | | 1.52350e4 | 770.71164 | |

FIG. 13

Operator : Sequence row : 1
Instrument : Intrument 1 Position : Vial 14
Date of injection: 2018/8/10 15:13:35 Injection repetition : 1
Injection volume : 5.000 µl
Acquisition method : D: \CHEM32\1\DATA\HDP107\HDP107 2018-08-10 15-12-05\HDP107-G-CHIRAL.M
Last revised : 2018/8/9 20:33:04
Last revised : 2018/8/6 9:57:51
(Revised after retrieval)
Additioinal Info.: Peaks have been manually integrated

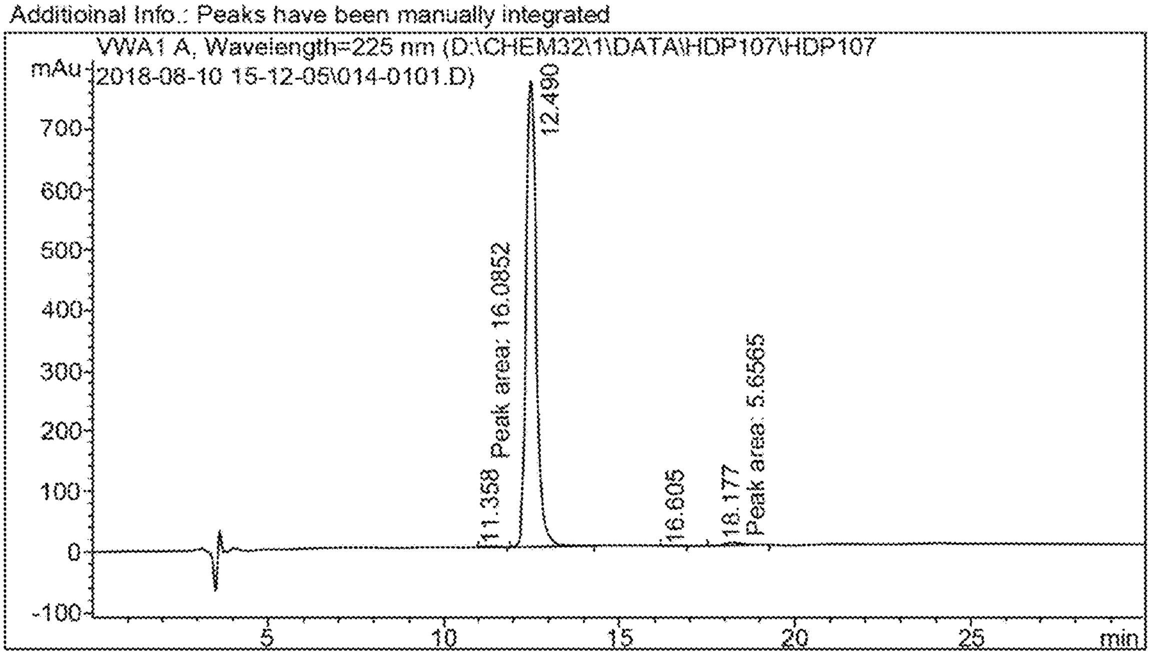

==================================================
Report for area percentage
==================================================

Sequence : Signal
Produce factor : 1.0000
Dilution factor : 1.0000
Product factor and dilution factor
for internal standard Signal 1: VWD1 A, Wavelength=225 nm

| Peak # | RT. [min] | Type | Peak width [min] | Peak Area [mAu*s] | Peak Height [mAu] | Peak area % |
|---|---|---|---|---|---|---|
| 1 | 11.358 | MM | 0.3755 | 16.08519 | 7.13889e-1 | 0.1056 |
| 2 | 12.490 | BB | 0.3026 | 1.52430e4 | 764.45221 | 98.7400 |
| 3 | 16.605 | MM | 0.2901 | 5.65650 | 2.36611e-1 | 0.0371 |
| 4 | 18.177 | BB | 0.4771 | 170.22444 | 5.30892 | 1.1173 |
| Total: | | | | 1.52350e4 | 770.71164 | |

FIG. 14

| n | Mean | Standard Deviation | Max. | Min. |
|---|---|---|---|---|
| 5 | -18.269 | 0.0000 | -18.269 | -18.269 |

| S.No | Time | Result | Scale | OR°Arc | WLG.nm | Lg.mm | Conc.g/100ml | Temp. |
|---|---|---|---|---|---|---|---|---|
| 1 | 15:27:12 | -18.269 | SR | -0.094 | 589 | 100.00 | 0.514 | 25.0 |
| 2 | 15:27:21 | -18.269 | SR | -0.094 | 589 | 100.00 | 0.514 | 25.0 |
| 3 | 15:27:30 | -18.269 | SR | -0.094 | 589 | 100.00 | 0.514 | 25.0 |
| 4 | 15:27:40 | -18.269 | SR | -0.094 | 589 | 100.00 | 0.514 | 25.0 |
| 5 | 15:27:49 | -18.269 | SR | -0.094 | 589 | 100.00 | 0.514 | 25.0 |

METHOD FOR PREPARING INTERMEDIATE FOR USE IN SYNTHESIS OF FLORFENICOL AND COMPOUNDS PREPARED THEREBY

CROSS REFERENCE TO RELATED APPLICATION

This application is a 371 of PCT/CN2020/107352, filed Aug. 6, 2020, and further claims the priority of Chinese Patent Application No. 202010184089.7, entitled "Method for preparing intermediate for use in synthesis of florfenicol and compounds prepared thereby" filed with the China National Intellectual Property Administration on Mar. 16, 2020, the entire content of which is incorporated in this application by reference.

TECHNICAL FIELD

The present invention belongs to the technical field of drug synthesis. And the present invention and relates to a method for preparing the intermediate D-p-methylsulfonyl phenylserine ester of florfenicol, and to two compounds obtained during the process of preparing the intermediate.

BACKGROUND

Florfenicol, also named thiamphenicol, has an alternate name of fluprofen in China. Thiamphenicol is a chloramphenicol-based broad-spectrum antibacterial drug dedicatedly used in veterinary medicine, which was successfully developed by Schering-Plough in the US in late 1980s. The florfenicol has an antibacterial activity against sensitive bacteria similar to chloramphenicol and thiamphenicol, but florfenicol is also sensitive to the bacteria that are resistant to chloramphenicol and thiamphenicol. Florfenicol was registered with the US FDA in 1996 and was approved in China. In the prevention and treatment of diseases in animals, especially in food-producing animals, florfenicol has a wide range of prospective applications.

Florfenicol has a formula of $C_{12}H_{14}Cl_2FNO_4S$, a molecular weight of 358.2, and a chemical structure shown below:

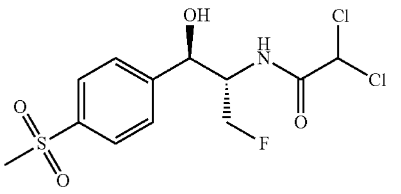 [SMILES: CS(=O)(=O)c1ccc([C@@H](O)[C@@H](CF)NC(=O)C(Cl)Cl)cc1]

At present, well-developed processes involve the use of 4-toluene sulfonyl chloride as the starting material to form p-methylsulphonyl benzaldehyde after a reduction reaction, a methylation reaction, a bromo-oxidation reaction and a hydrolysis reaction, and the p-methylsulfonyl benzaldehyde was reacted with glycine and copper(II) sulfate to form a copper salt, and the copper salt is subsequently subject to an esterification reaction and to resolution with tartaric acid to form an intermediate of D-p-methyl sulfone phenyl ethyl serinate, then D-p-methyl sulfone phenyl ethyl serinate is subject to a reduction reaction and to a reaction with dichloroacetonitrile to form an oxazoline compound, and the oxazoline compound is subject to a fluorination reaction and a hydrolysis reaction to give florfenicol. The reaction route for this process is showed as follows.

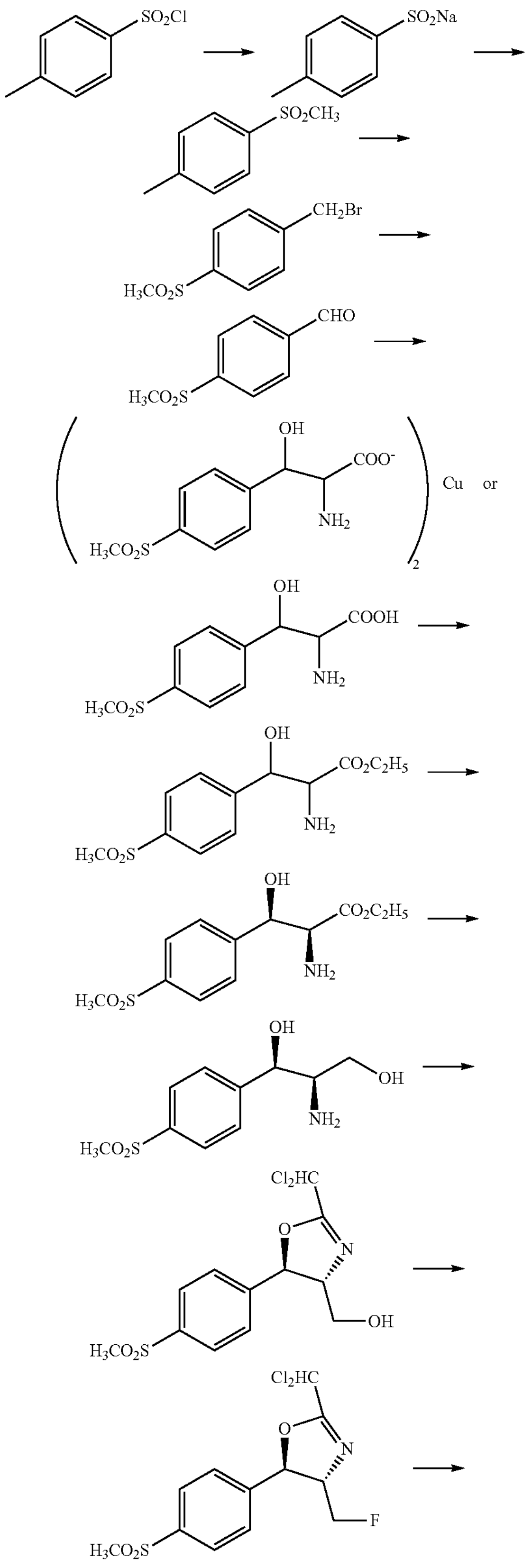

-continued

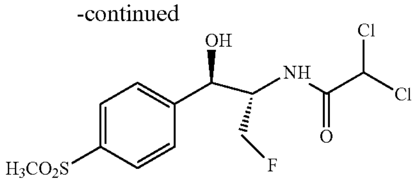

This route involves resolution of racemic D- and L-ethyl serinate, and one of the isomers is discarded, causing a waste of 50% of the starting materials and an increase in the manufacturing costs. Besides, a large amount of waste water of copper (II) sulfate is generated during preparation of the copper salt, which leads to a very high cost for waste water treatment and to a high environmental pressure.

In traditional synthetic processes, many by-products are formed and a low conversion rate is obtained due to the structural asymmetry of the functional groups at the chiral carbon, which leads to an increase in the cost of active pharmaceutical ingredient. Therefore, the key to reduce cost is to increase the conversion rate. The synthesis of chiral drugs requires the use of asymmetric synthesis technologies such as chiral catalysts, asymmetric catalytic synthesis, 3 new chiral pool methods, etc., in order to improve technical aspects of the prior products and even to reduce production costs dramatically and enhance market competitiveness.

SUMMARY

This application is proposed to address the issues present in the prior arts in which low chiral resolution yield, large waste of raw materials, high production cost, and high environmental cost caused by generation of a large amount of copper sulfate waste water during the preparation of copper salt, as well as excessively high cost for waste water treatment when synthesizing D-p-methylsulfonyl phenylserine ester.

Chiral D-p-methylsulfonyl phenylserine ester is obtained in the present invention via direct synthesis, avoiding the drawbacks in the prior arts.

The method for preparing intermediate TM of florfenicol provided in the present invention comprises the following synthetic route:

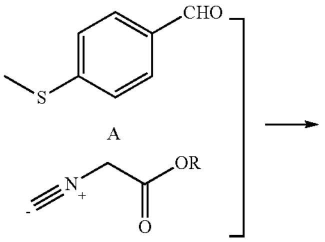

A

B

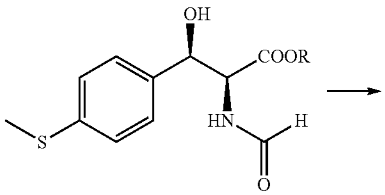

C

-continued

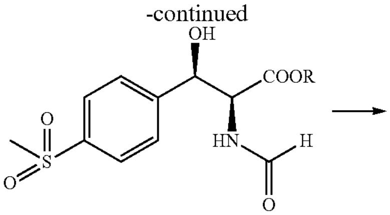

D

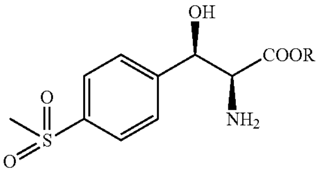

TM wherein R is selected from methyl, ethyl, propyl, isopropyl, butyl, isobutyl, tert-butyl;

and the method comprises steps of:

dissolving compound A (4-methylthiobenzaldehyde) and compound B (isocyanoacetate) in a first organic solvent, adding a chiral catalyst to proceed a catalysis reaction; performing workup by adding a first acid after the catalysis reaction is ended; filtering out the precipitated solids (isomer of compound C) after the workup, and concentrating the filtrate under reduced pressure to give compound C;

oxidizing compound C to compound D by using an oxidant;

removing the formyl group in compound D to give the intermediate of florfenicol—compound TM;

wherein in step (1), the chiral catalyst has a structure represented by Formula 1:

Formula 1

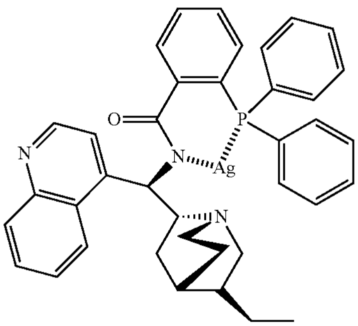

wherein M is selected from Au, Ag, or Cu;

$R_1$ is selected from methoxy, chlorine atom, or is absent;

$R_2$ is selected from methyl, phenyl, or is absent;

$R_3$ is selected from methyl, phenyl, or is absent.

Specifically, examples of the chiral catalyst in the present invention are as follows:

M is Au, $R_1$ is methoxy; $R_2$ is methyl; $R_3$ is methyl;

M is Au; $R_1$ is a chlorine atom; $R_2$ is a methyl group; $R_3$ is a methyl group.

M is Au or Cu; $R_1$ is absent; $R_2$ is phenyl; $R_3$ is tolyl.

M is Ag; $R_1$ is methoxy; $R_2$ is methyl; $R_3$ is methyl.

M is Ag; $R_1$ is a chlorine atom; $R_2$ is a methyl group; $R_3$ is a methyl group.

M is Ag; $R_1$ is absent; $R_2$ is phenyl; $R_3$ is phenyl.

M is Ag; $R_1$ is absent; $R_2$ is absent; $R_3$ is absent.

M is Ag; $R_1$ is a chlorine atom; $R_2$ is a phenyl group; $R_3$ is absent.

M is Cu; $R_1$ is methoxy; $R_2$ is methyl; $R_3$ is methyl.

M is Cu; $R_1$ is a chlorine atom; $R_2$ is a phenyl group; $R_3$ is a phenyl group.

M is Cu; $R_1$ is methoxy; $R_2$ is phenyl; $R_3$ is methyl.

M is Cu; $R_1$ is absent; $R_2$ is absent; $R_3$ is absent.

In the method of the present invention, a "one-pot method" is used in the first step of reaction. Under the catalysis of the chiral catalyst, compound A and compound B are subject to a catalysis reaction and subsequently a reaction under acidic conditions to form compound C having two chiral centers.

In step (1) of the preparation method of the present invention, the molar ratio of compound A to compound B is 1:1. Due to the high-efficiency catalysis by the catalyst in the invention, compound A and compound B can be completely converted in a molar feeding ratio of 1:1, thereby reducing the waste of raw materials.

In the step (1) of the preparation method of the present invention, the amount of the catalyst compound A of 0.1%-0.5 wt % with respect to compound A. Due to the efficient catalytic performance of the catalyst of the present invention, the amount of the catalyst only accounts for a small part of the raw material.

Preferably, in step (1) of the preparation method of the present invention, the first organic solvent is selected from one or more of tetrahydrofuran, dichloromethane, tert-butanol, ethyl acetate, acetonitrile, 1,4-dioxane and methyl tert-butyl ether. In step (1), the organic solvent can be selected from commonly used organic solvents. The solvent has low cost and low toxicity, which is very suitable for industrial production.

In the step (1) of the preparation method of the present invention, the first acid added is not particularly limited, and the acids commonly used in the industry, such as hydrochloric acid, sulfuric acid, and etc. can be used. Preferably, the first acid is selected from one or more of hydrochloric acid, phosphoric acid, boric acid, carbonic acid, sulfuric acid, and nitric acid. Addition of the first acidic acid will facilitate the completion of the reaction.

With respect to the reaction temperature after addition of the catalyst in step (1), since the catalysis reaction is slightly exothermic, the temperature is controlled at room temperature. Excessively low temperature is not conducive to the progress of the reaction, while high temperature will cause generation of by-products.

In step (2) of the preparation method of the present invention, the oxidation of compound C to compound D can be accomplished by a well-developed methods in the prior art. In one embodiment of the present invention, compound C is oxidized to compound D by the following process: dissolving compound C in a second organic solvent, adding EDTA (ethylenediaminetetraacetic acid) and the oxidant, reaction is conducted by controlling the reaction temperature within a range of from 40° C. to 60° C. to give compound D.

Preferably, in step (2) of the preparation method of the present invention, the second organic solvent is selected from one or more of methanol, ethanol, glycerol, and isopropanol.

Preferably, in step (2) of the preparation method of the present invention, the oxidant is selected from one or more of potassium permanganate, $MnO_2$, m-chloroperoxybenzoic acid, and hydrogen peroxide.

More preferably, in step (2) of the preparation method of the present invention, the oxidant is hydrogen peroxide, and the mass ratio of compound C, hydrogen peroxide to EDTA is 1:0.85-1.0:0.005-0.01.

In step (3) of the preparation method of the present invention, the removal of the formyl group in compound D can be accomplished by a well-developed method in the prior art. In one embodiment of the present invention, the formyl group in compound D is removed by the following process: dissolving compound D in a third organic solvent, adding a second acid to react, and after the reaction is ended, adding an alkali to adjust pH value until white solids are precipitated, giving the intermediate TM of florfenicol.

Preferably, in step (3), the third organic solvent is selected from one or more of methanol, ethanol, glycerol, and isopropanol.

Preferably, in step (3), the mass ratio of compound D to the second acid is 1:0.4-0.8.

More preferably, in step (3), the second acid is selected from one or more of hydrochloric acid, phosphoric acid, boric acid, carbonic acid, sulfuric acid, and nitric acid.

Further preferably, in step (3), the alkali is selected from one or more of sodium hydroxide, potassium hydroxide, potassium carbonate, sodium carbonate, sodium bicarbonate, and ammonia. The purpose of addition of the alkali is to adjust the pH to the range of 7.5-8 so that the product can be precipitated. The alkali to achieve this goal can be a common alkali. Considering the yield and the raw material cost, the pH value adjusted by adding alkali should not be too high, and it is better that the pH reaches 7.5-8 at which a large amount of solids precipitate.

By adopting the method for preparing the intermediate of florfenicol of the present invention, the following technical effects can be achieved.

The chiral center of the intermediates TM of florfenicol is directly formed by the first step, the there was no need for chiral resolution in subsequent steps to obtain the intermediate TM of florfenicol. In the first step of the reaction for the preparation of compound C i, the chiral compound C is obtained in a yield of 75%-80%, which is significantly higher than the yield obtained (about 40%) through the conventional resolution process, and the product has a high chiral purity. In addition, no anhydrous copper sulfate that pollutes the environment is used in the method of the present invention, thereby alleviating the environmental pressure.

In the preparation method of the present invention, the two compounds, compound A and compound B, are used as raw materials for the reaction, which has higher material availability and synthesis efficiency than linear synthesis methods, and has less overall process operations.

After preparing the intermediate TM of florfenicol by using the method of the present invention, florfenicol can be synthesized by the existing common synthetic methods. There are many well-developed methods for synthesizing florfenicol through florfenicol intermediate TM, and these methods have been reported in many existing literatures. The synthesis of florfenicol by florfenicol intermediate TM can refer to patent documents CN106278964A, CN101265220A and the like.

The present invention also provides compounds having a structure represented by formula (2) and formula (3):

Formula (2)

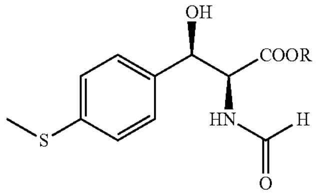

Formula (3)

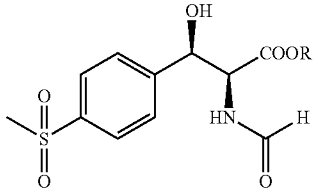

In Formula 2 or Formula 3, R is selected from methyl, ethyl, propyl, isopropyl, butyl, isobutyl, and tert-butyl.

DESCRIPTION OF THE DRAWINGS

FIG. 13 is the chiral HPLC spectrum of compound D-3 (isopropyl ester) obtained by the preparation method of the present invention;

FIG. 14 is the chiral HPLC spectrum of intermediate TM-3 (isopropyl ester) obtained by the preparation method of the present invention;

DETAILED DESCRIPTION OF THE EMBODIMENTS

The present invention will be described in detail hereafter in conjunction with the examples.

The structure of the chiral catalyst used in the following examples is as follows:

Formula 1-1

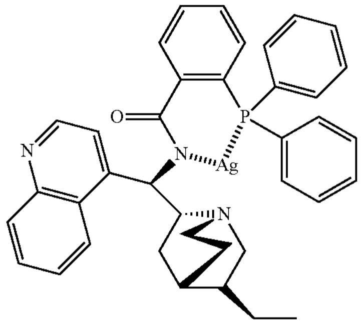

Example 1

Synthesis of Compound C-1 (Methyl Ester)

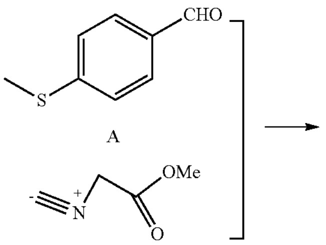

A

B-1

-continued

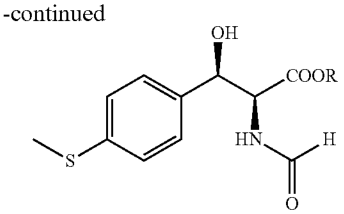

C-1

In a reactor were added sequentially 700 g of ethyl acetate, 100 g of compound A, and 0.1 g of catalyst represented by Formula 1-1. The resulting mixture was stirred for about 10 minutes while the reaction system temperature was controlled at 15° C.-20° C. and 65 g of compound B-1 was dissolved in ethyl acetate. The solution of compound B-1 in ethyl acetate was slowly dripped into the reactor, with the dripping time controlled within about 0.5 hour. A slight exotherm was observed. After the dripping was completed, the reaction was continued for 1 hour. The reaction mixture was sampled and monitored for completion of the reaction, and a workup was followed. To the reaction solution was added 5 wt % $H_2SO_4$, heated to 45° C. and stirred for 1 hour. TLC was performed and completion of the hydrolysis was detected. Filtration was conducted to remove insoluble matters, and the filtrate was then reduced to dryness by removing the solvent under reduced pressure, giving 143 g of compound C-1 in a yield of 80.9%.

Figure 1:
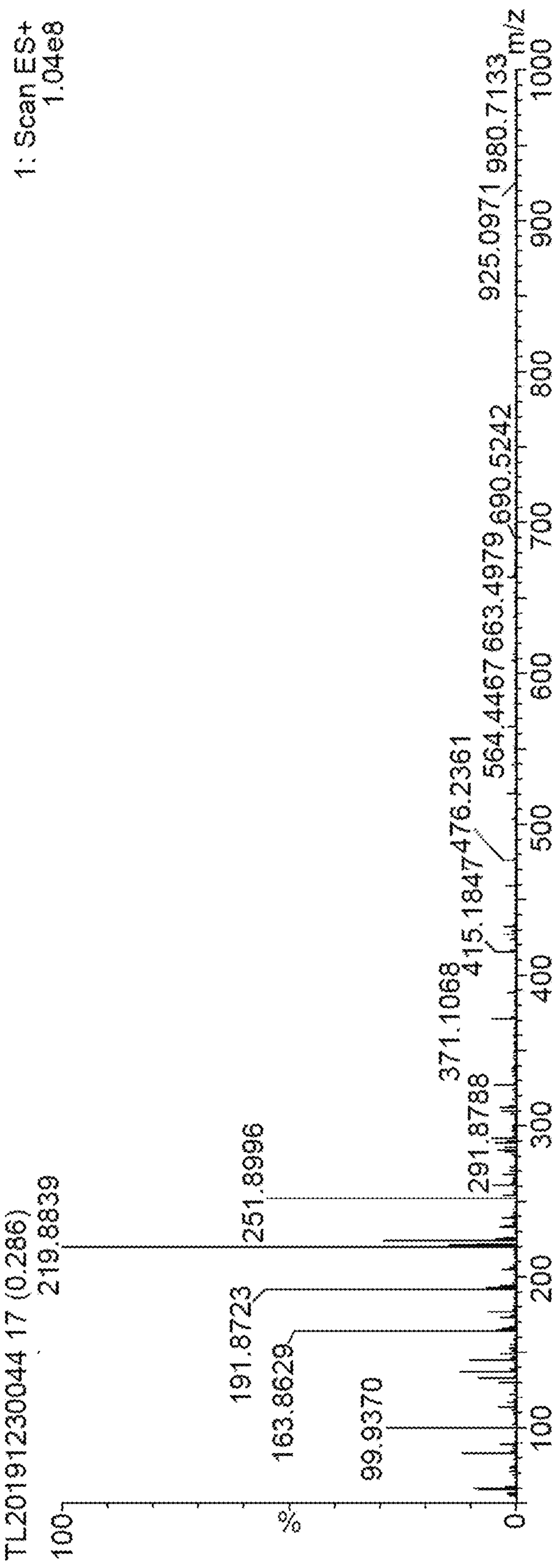
FIG. 1 is the mass spectrum of compound C-1 (methyl ester) obtained by the preparation method of the present invention.
Figure 1:
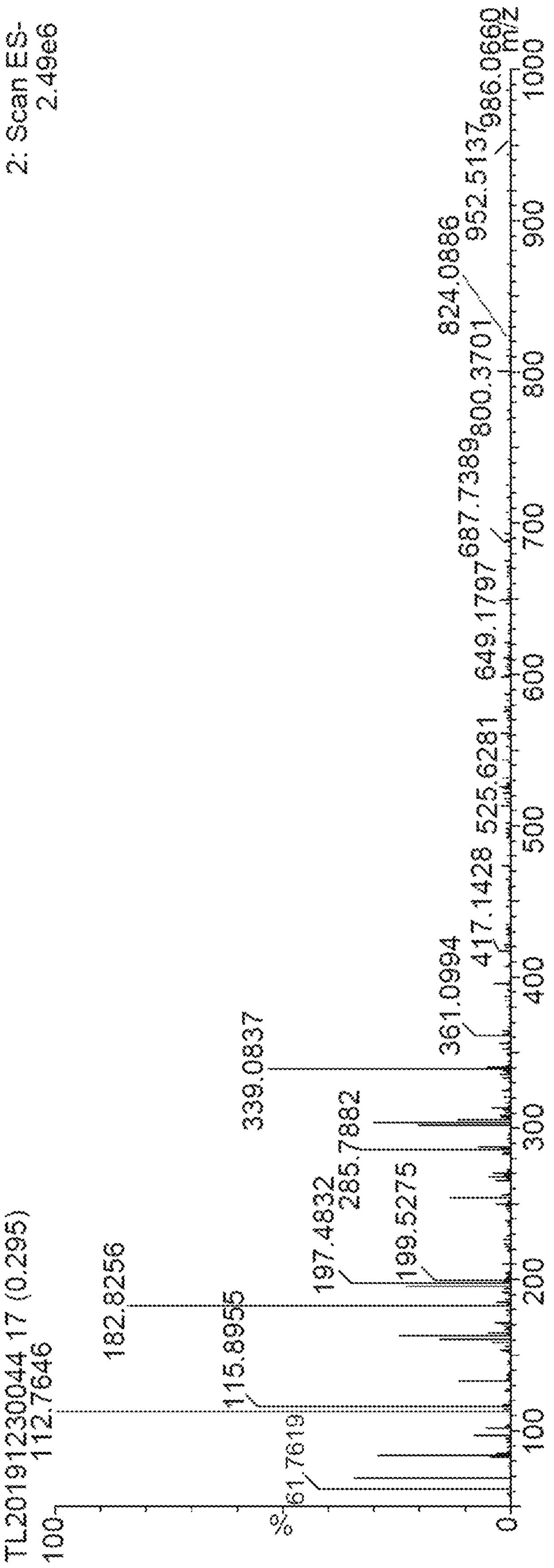
Figure 2:
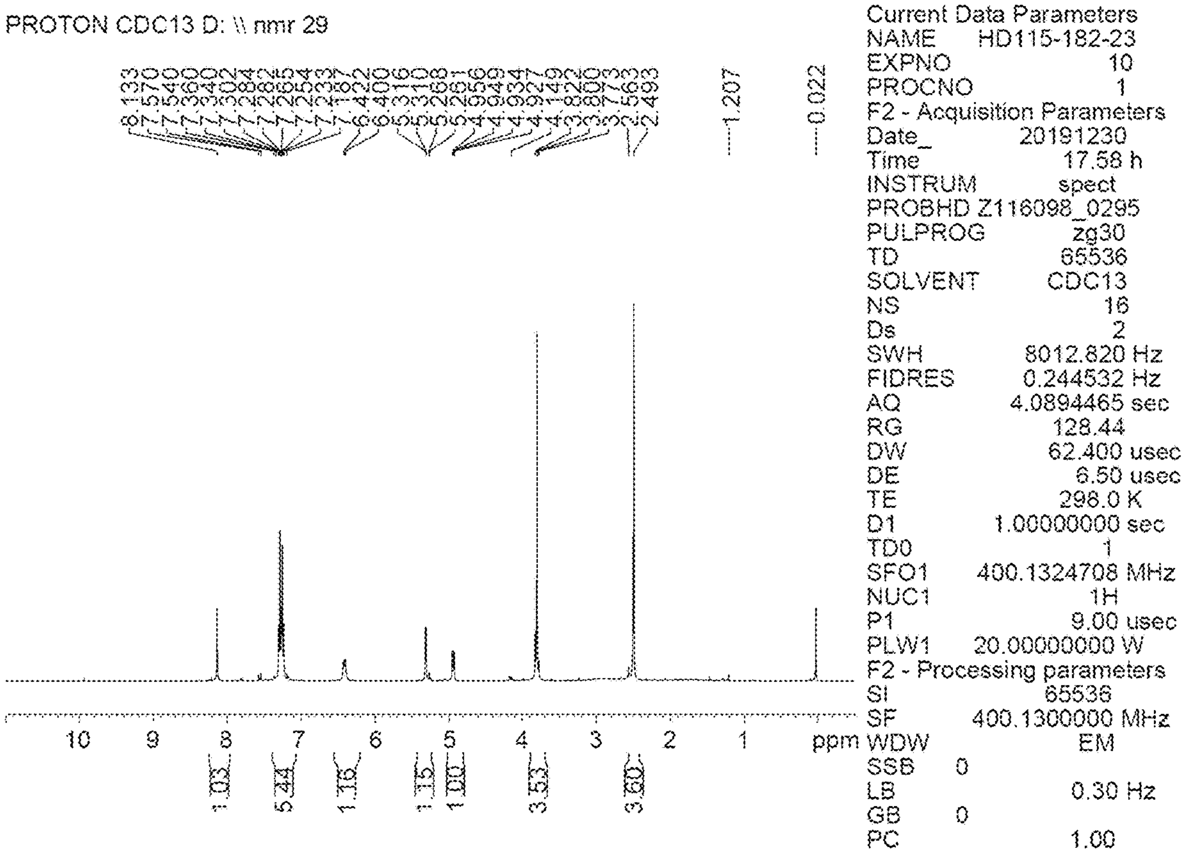
FIG. 2 is the $^1$H NMR spectrum of compound C-1 (methyl ester) obtained by the preparation method of the present invention.
Figure 3:
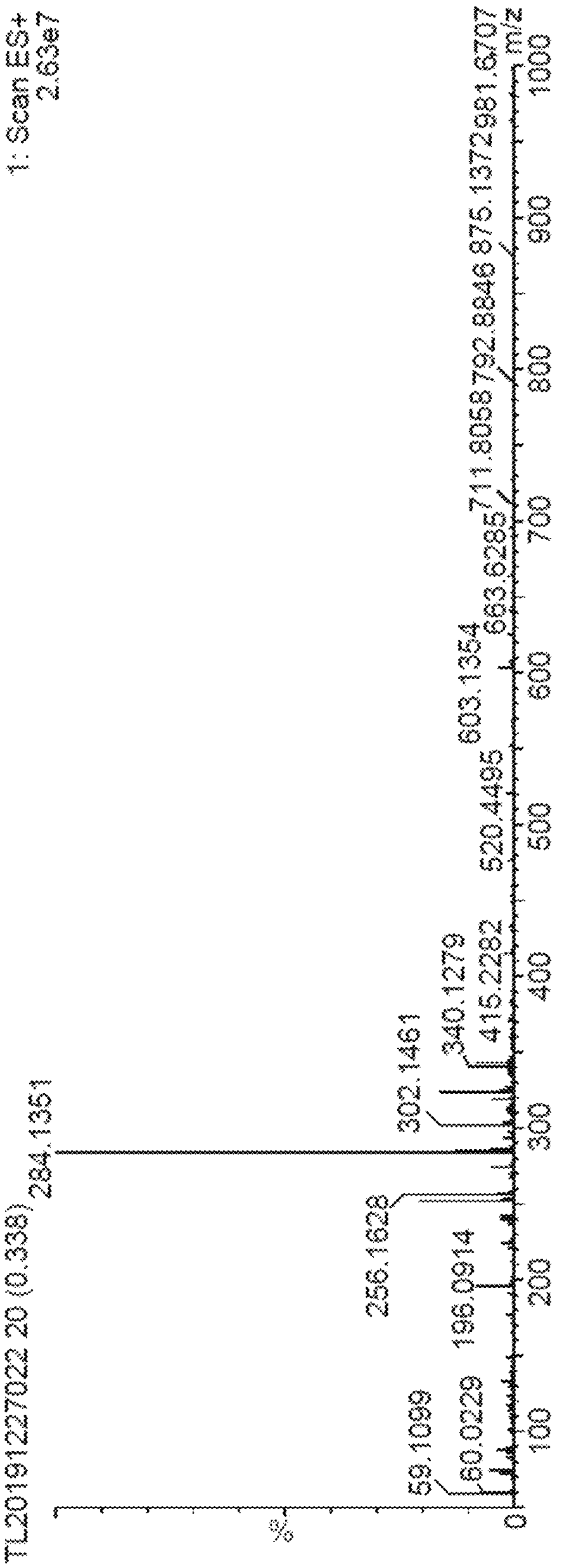
FIG. 3 is the mass spectrum of compound D-1 (methyl ester) obtained by the preparation method of the present invention.
Figure 3:
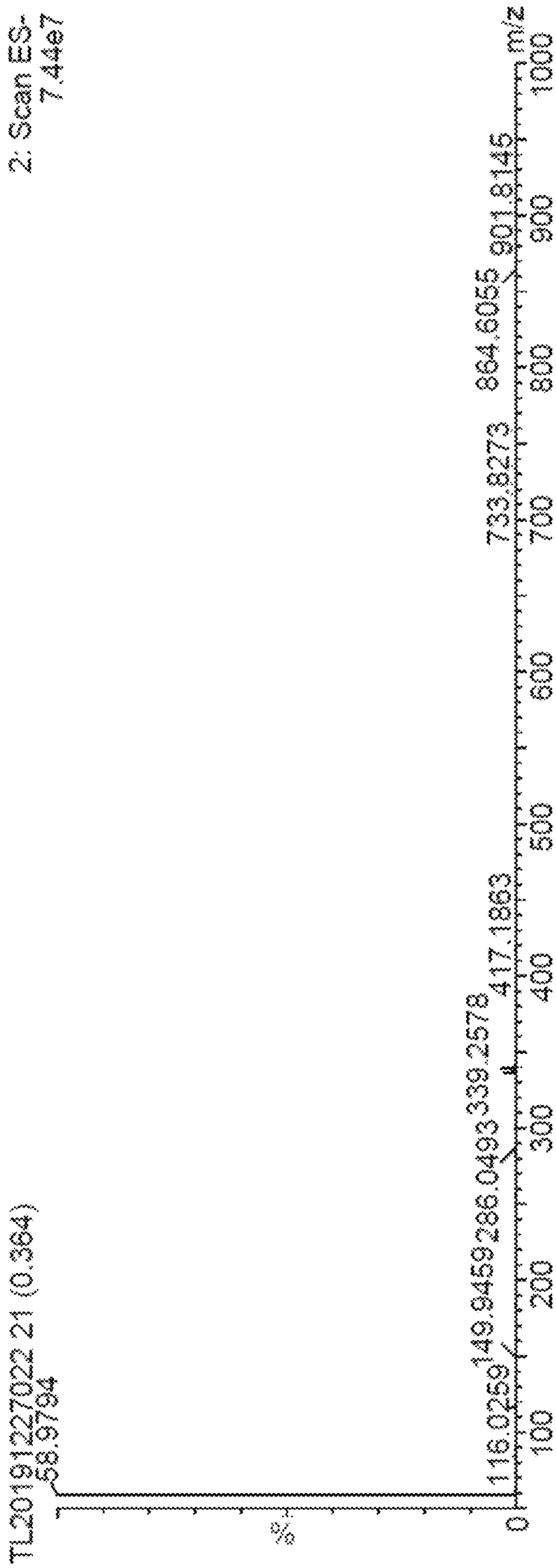
Figure 4:
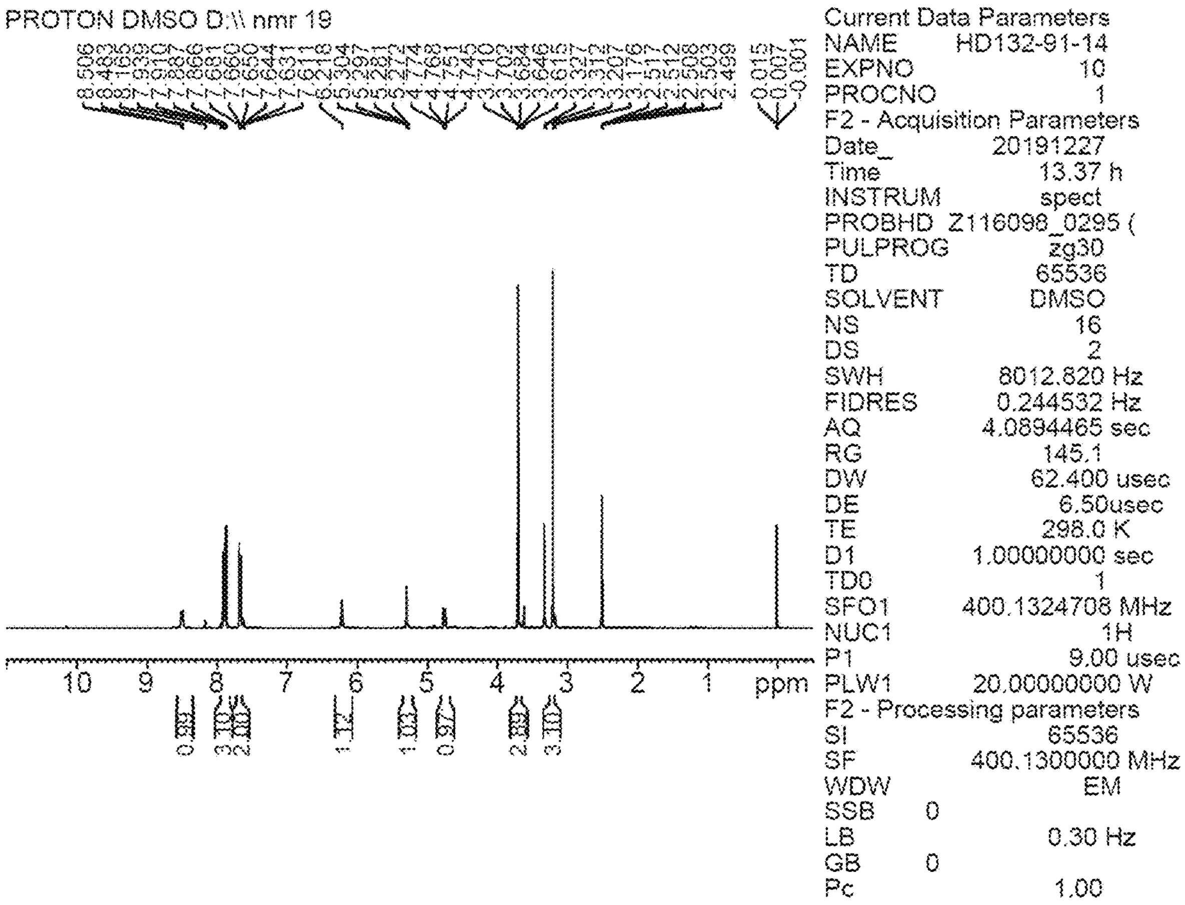
FIG. 4 is the $^1$H NMR spectrum of compound D-1 (methyl ester) obtained by the preparation method of the present invention.
Figure 5:
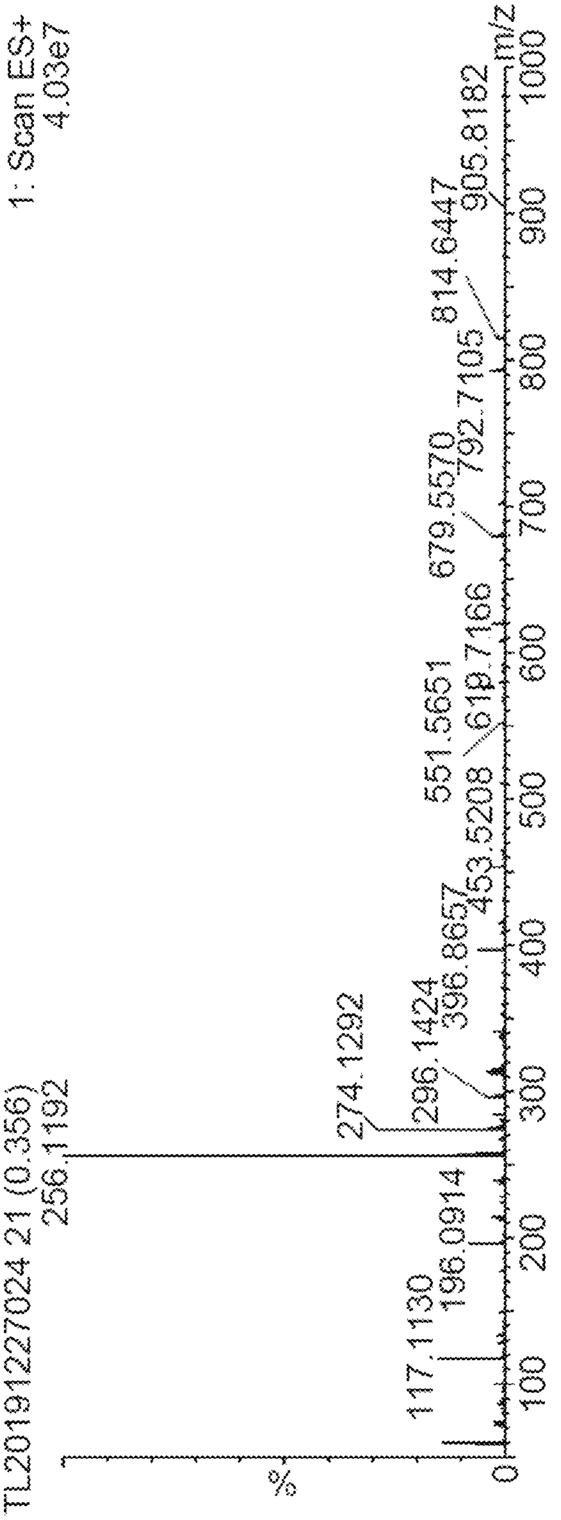
FIG. 5 is the mass spectrum of intermediate TM-1 (methyl ester) obtained by the preparation method of the present invention.
Figure 5:
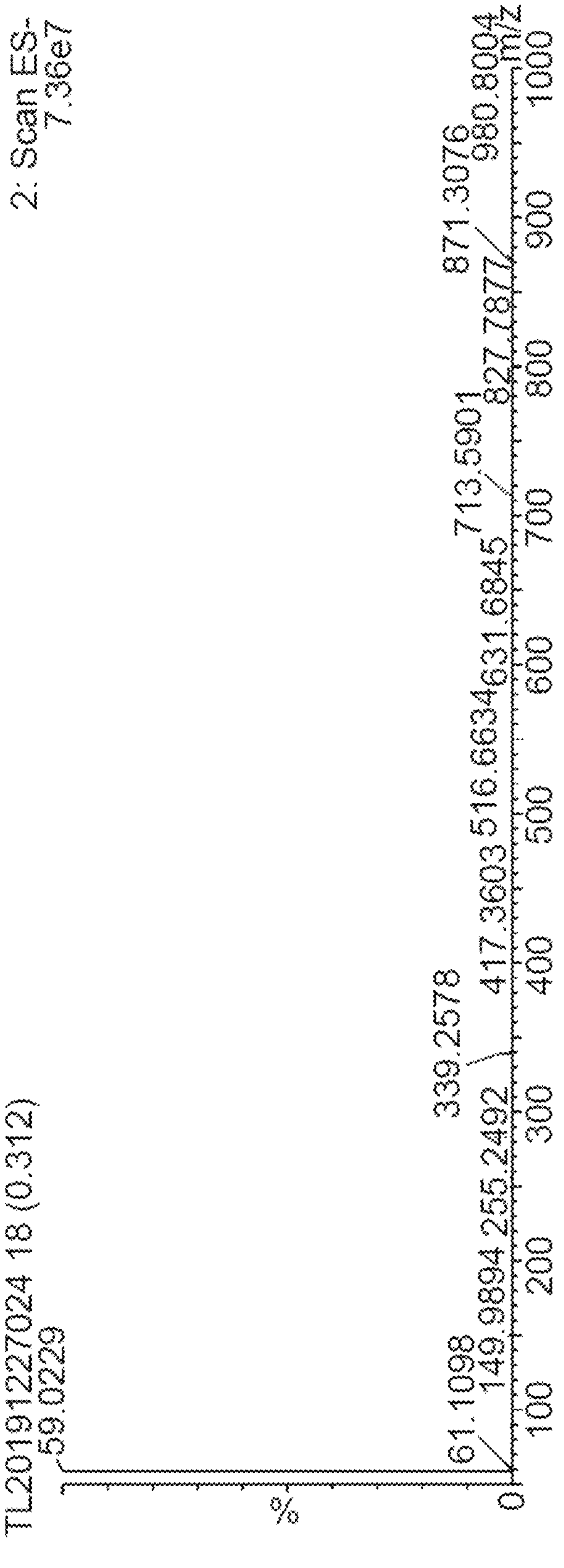
Figure 6:
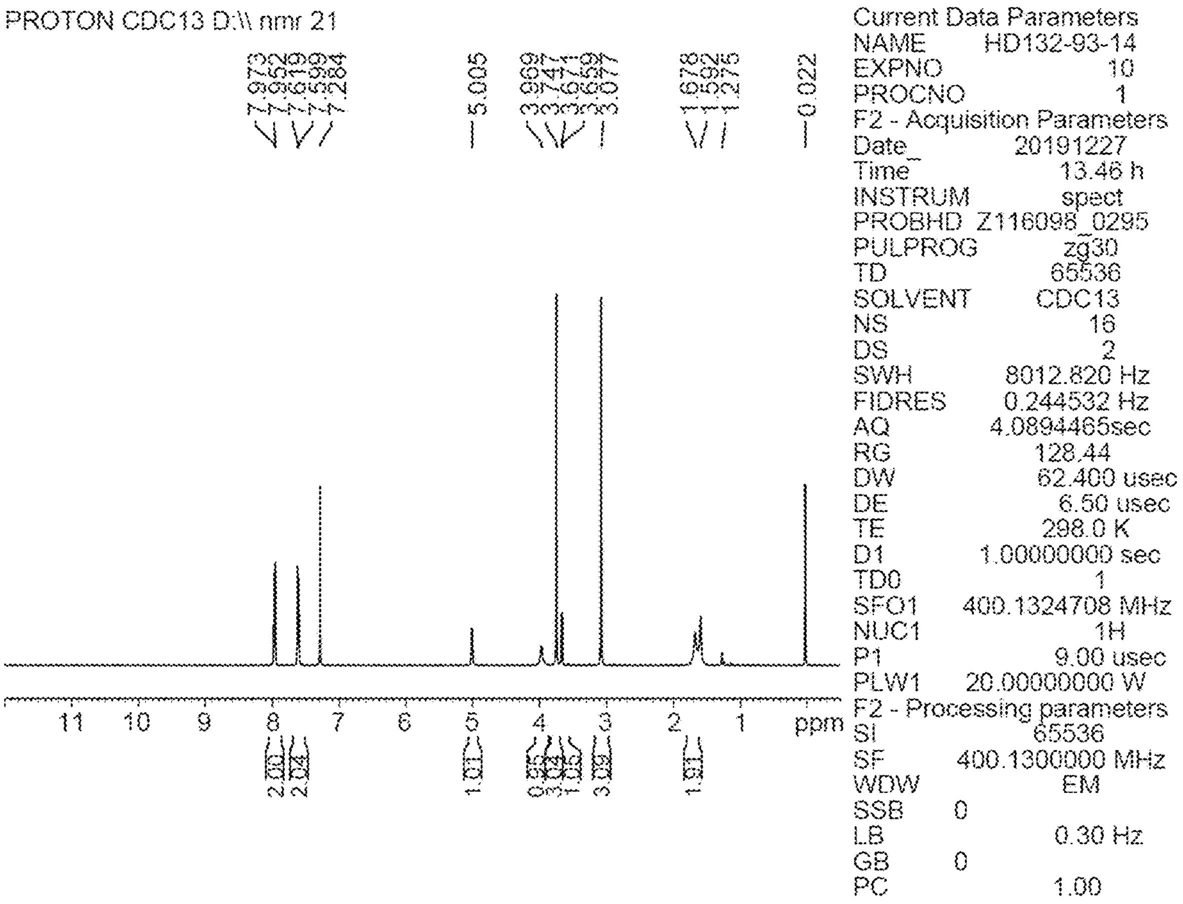
FIG. 6 is the $^1$H NMR spectrum of the intermediate TM (methyl ester) obtained by the preparation method of the present invention.

The mass spectrum of compound C-1 (methyl ester) is shown in FIG. 1, and its $^1$H NMR spectrum is shown in FIG. 2.

Synthesis of Compound D-1 (Methyl Ester)

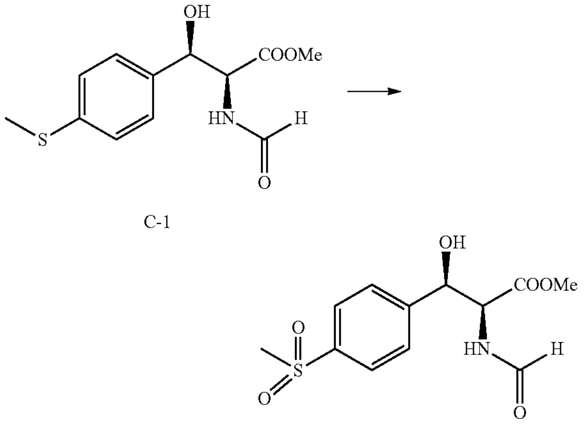

C-1

D-1

In a reactor were added sequentially 100 g of C-1, 0.6 g of EDTA, 300 g of methanol, the resulting mixture was heated to 45° C. and stirred. Ninety grams (90 g) of m-chloroperoxybenzoic acid was slowly added dropwise while controlling the temperature at 45° C.-55° C., and the dripping was finished within about 1 hour. Reaction was lasted for 6-8 hours when the temperature was maintained. Sampling and monitoring were conducted, and the reaction was terminated when the remaining starting material of C-1 was less than or equal to 1%. The reaction solution was transferred to a concentration reactor and concentrated under reduced pressure, the internal temperature was controlled at 40° C.-60° C., and the concentration was conducted until there was almost no methanol remaining, and the distillation was terminated. Then tap water was added to the reactor, and the temperature was lowered to 10° C.-20° C. and held for 1 hour. Crystal precipitation was conducted when the temperature was maintained. The crystals were discharged and centrifuged to give 81 g of compound D-1 in a yield of 72.4%.

Synthesis of Intermediate TM-1 of Florfenicol(Methyl Ester)

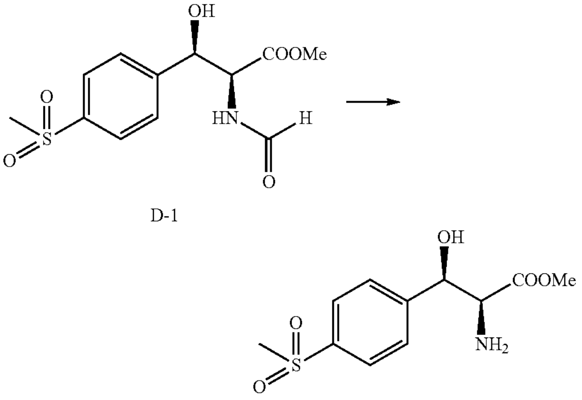

D-1

TM-1

In a reactor were added sequentially 300 g of methanol, 100 g of D-1 and 80 g of carbonic acid, the temperature of the resulting mixture was increased to 50° C., and the reaction was conducted for 4 hours while the temperature was maintained. Sampling and monitoring were conducted, and the reaction was terminated when the remaining starting material of compound D-1 was less than 1%. Concentration was initiated under reduced pressure while the internal temperature was controlled at 40° C.-60° C. Distillation was continued until there was no remaining methanol. Then water and activated carbon were added to remove insoluble substances, the filtrate was cooled to a temperature below 15° C., ammonia was slowly added dropwise, pH was adjusted to 7.5-8, and a large amount of white solids precipitated. After adjustment of pH, the mixture was cooled to 0° C.-5° C. Crystal growth was conducted for 2 hours while the temperature was maintained. The mixture was discharged into a scraper centrifuge and rotation filtering was followed. The filter cake was rinsed with water and dried to give 78 g of compound TM-1 in a yield of 86%.

Example 2

Synthesis of Compound C-2 (Ethyl Ester)

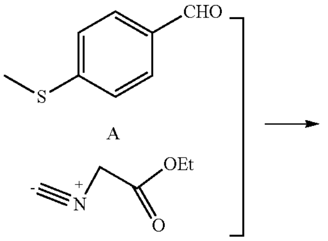

A

B-2

-continued

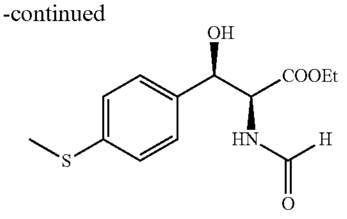

C-2

In a reactor were added sequentially 7000 g of tetrahydrofuran, 1000 g of compound A, and 4 g of catalyst represented by Formula 1-1. The resulting mixture was stirred for about 10 minutes while the temperature of reaction system was controlled at 15° C.-20° C. and 723 g of compound B-2 was dissolved in tetrahydrofuran. The solution of compound B-2 in tetrahydrofuran was slowly dripped into the reactor, with the dripping time controlled within about 0.5 hour. A slight exotherm was observed. After the dripping was completed, the reaction was continued for 1 hour. The reaction mixture was sampled and monitored for completion of the reaction, and workup was followed. To the reaction solution was added 5 wt % $H_2SO_4$, heated to 45° C. and stirred for 1 hour. TLC was performed and completion of the hydrolysis was detected. Filtration was conducted to remove insoluble matters, and the filtrate was reduced to dryness by removing the solvent under reduced pressure, giving 1563 g of compound C-2 in a yield of 84%.

Figure 7:
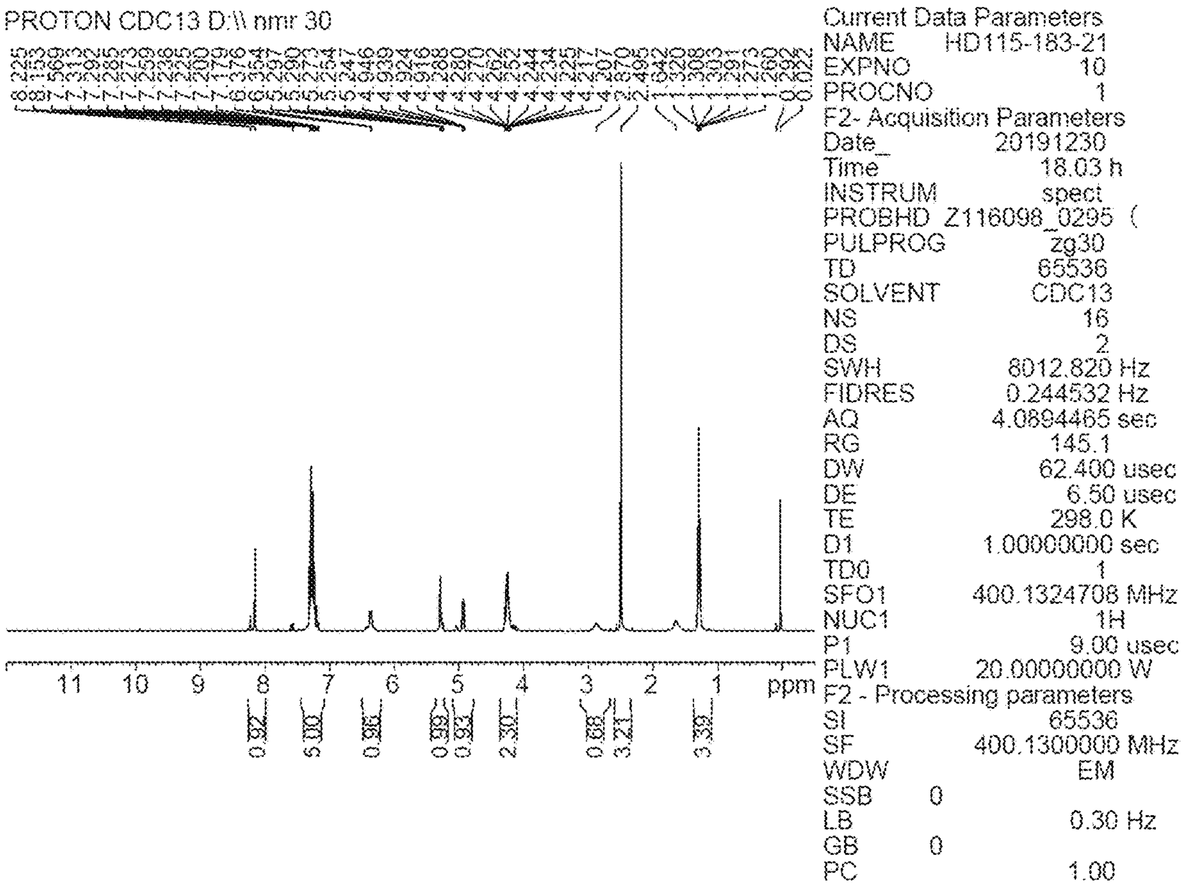
FIG. 7 is the $^1$H NMR spectrum of compound C-2 (ethyl ester) obtained by the preparation method of the present invention.

[mS+H]: 284.1, $^1$H NMR spectrum is shown in FIG. 7.

Synthesis of Compound D-2 (Ethyl Ester)

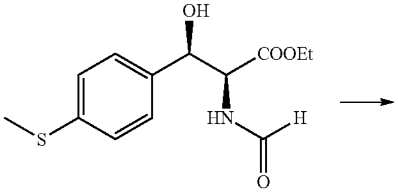

C-2

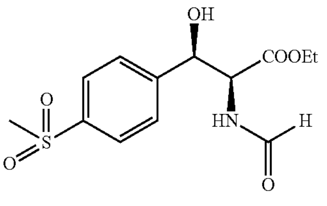

D-2

In a reactor were added sequentially 1000 g of C-2, 5 g of EDTA, 3000 g of methanol, the resulting mixture was heated to 45° C. and stirred. Nine hundred grams (900 g) of $H_2O_2$ (30 wt %) was slowly added dropwise while controlling the temperature at 45° C.-55° C., and the temperature was maintained for about 1 hour. Reaction was lasted for 6-8 hours. Sampling and monitoring were conducted, and the reaction was terminated when the remaining starting material of C-2 was less than or equal to 1%. The reaction solution was transferred to a concentration reactor and concentrated under reduced pressure, the internal temperature was controlled at 40° C.-60° C., and the concentration was conducted until there was almost no methanol remaining, and the distillation was terminated. Then tap water was added to the reactor, and the temperature was lowered to 10-20° C. and held for 1 hour. Crystal precipitation was conducted when the temperature was maintained. The crystals were discharged and centrifuged to give 789 g of compound D-2 in a yield of 70.9% (chemical purity: 98%).

Figure 8:
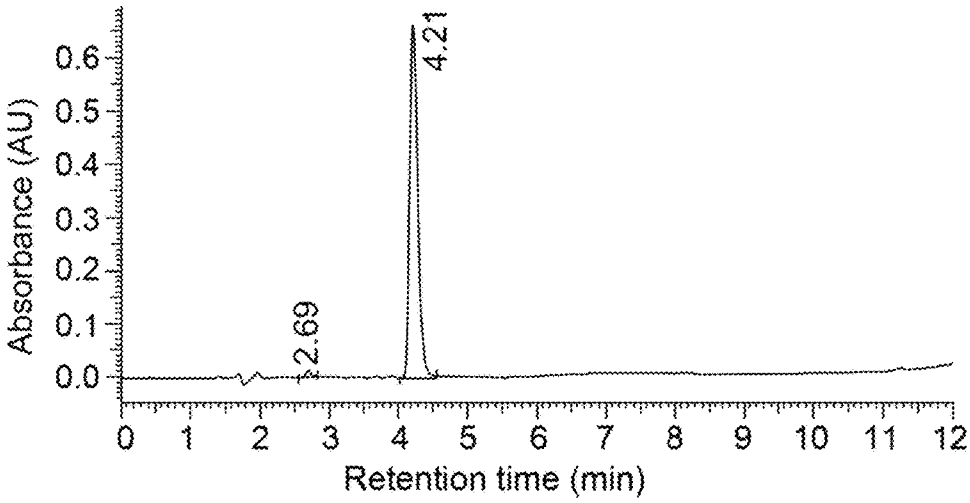
FIG. 8 is the HPLC spectrum of compound D-2 (ethyl ester) obtained by the preparation method of the present invention.
Figure 9:
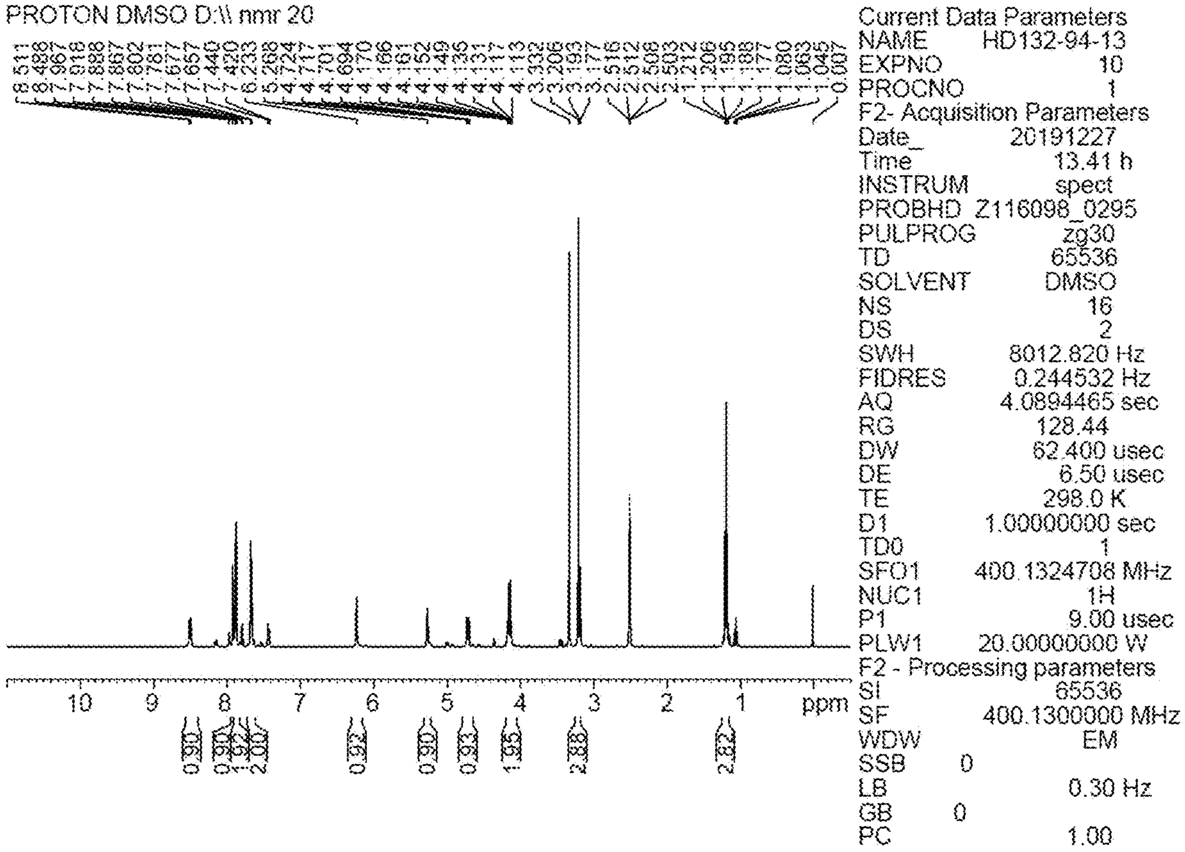
FIG. 9 is the $^1$H NMR spectrum of compound D-2 (ethyl ester) obtained by the preparation method of the present invention.

Characterization data of compound D-2: [MS+Na]: 338.1, its HPLC spectrum is shown in FIG. 8, and its $^1$H NMR spectrum is shown in FIG. 9.

Synthesis of Intermediate TM-2 (Ethyl Ester) of Florfenicol

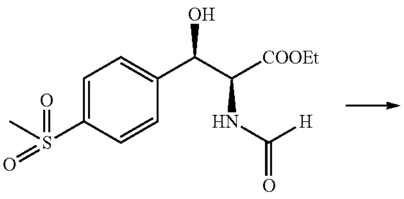

D-2

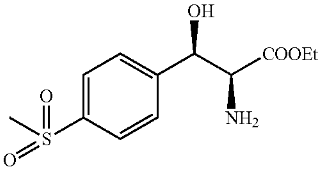

TM-2

In a reactor were added sequentially 3000 g of methanol, 1000 g of D-2 and 500 g of hydrochloric acid, the temperature of the resulting mixture was increased to 50° C., and the reaction was performed for 4 hours while the temperature was maintained. Sampling and monitoring were conducted, and the reaction was terminated when the remaining starting material of D-2 was less than 1%. Concentration was initiated under reduced pressure while the internal temperature was controlled at 40° C.-60° C. Distillation was continued until there was no remaining methanol. Then water and activated carbon were added to remove insoluble substances, the filtrate was cooled to a temperature below 15° C. Ammonia was slowly added dropwise, pH was adjusted to 7.5-8, and a large amount of white solids precipitated. After adjustment of pH, the temperature was cooled to 0° C.-5° C., crystal growth was conducted for 2 hours while the temperature was maintained. The mixture was discharged into a scraper centrifuge and rotation filtering was followed. The filter cake was rinsed with water and dried to give 838 g of compound TM-2 in a yield of 92%.

Figure 10:
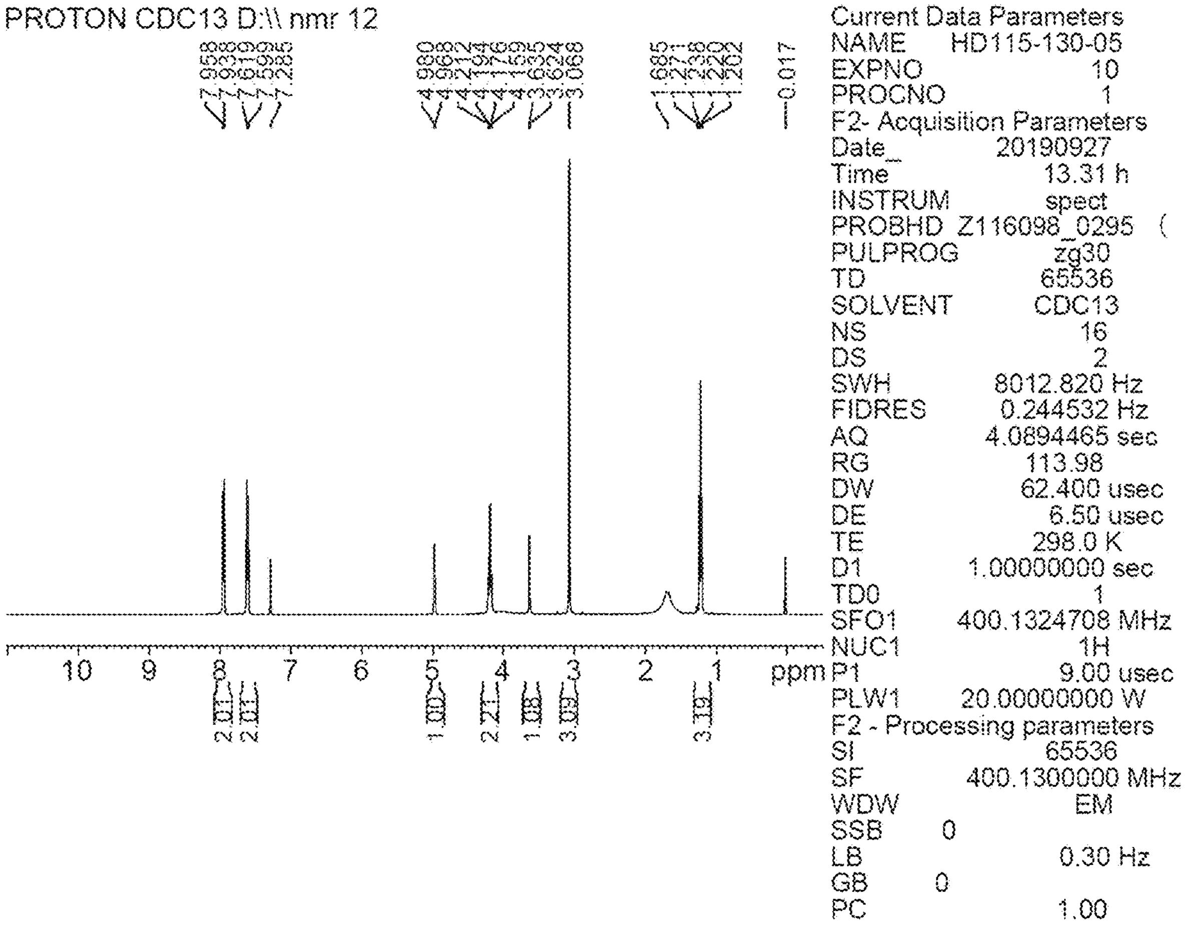
FIG. 10 is the $^1$H NMR spectrum of the intermediate TM-2 (ethyl ester) obtained by the preparation method of the present invention.

Characterization data of compound TM-2: [MS+H]: 288.2, and its $^1$H NMR spectrum is shown in FIG. 10.

Example 3

Synthesis of Compound C-3 (Isopropyl Ester)

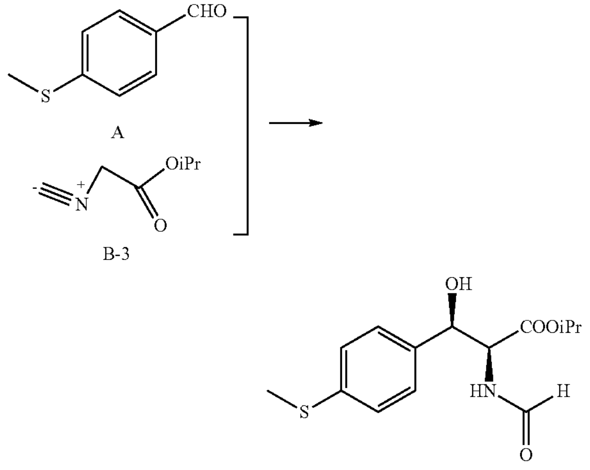

A

B-3

C-3

In a reactor were added sequentially 7000 g of dichloromethane, 1000 g of compound A, and 4.2 g of catalyst represented by Formula 1-1. The resulting mixture was stirred for about 10 minutes while the reaction system temperature was controlled at 15° C.-20° C. and 835 g of compound B-3 was dissolved in dichloromethane. The solution of compound B-3 in dichloromethane was slowly dripped into the reactor, with the dripping time controlled within about 0.5 hour. A slight exotherm was observed. After the dripping was completed, the reaction was continued for 1 hour. The reaction mixture was sampled and monitored for completion of the reaction, and workup was followed. To the reaction solution was added 5 wt % $H_2SO_4$, the reaction solution was heated to 45° C. and stirred for 1 hour. And then filtration was conducted to remove insoluble matters, and the filtrate was reduced to dryness by removing the solvent under reduced pressure, giving 1637 g of compound C-3 in a yield of 83.8%.

Figure 11:
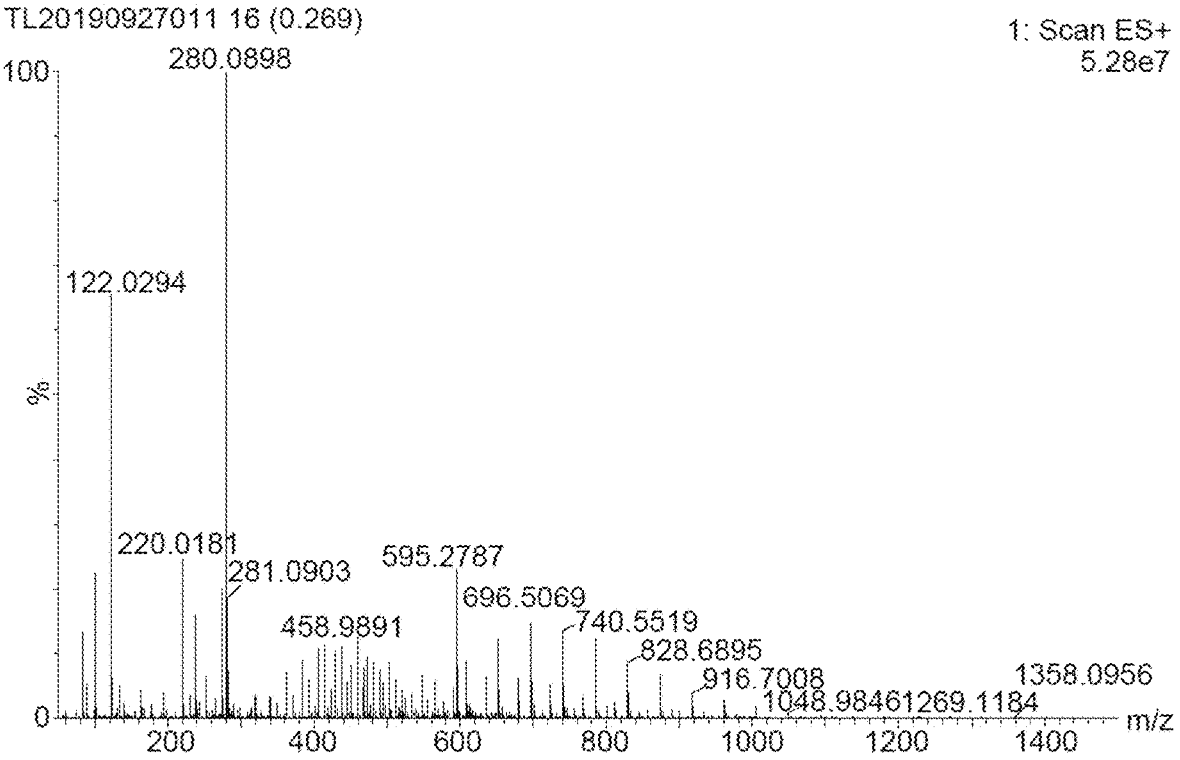
FIG. 11 is the mass spectrum of compound C-3 (isopropyl ester) obtained by the preparation method of the present invention.
Figure 11:
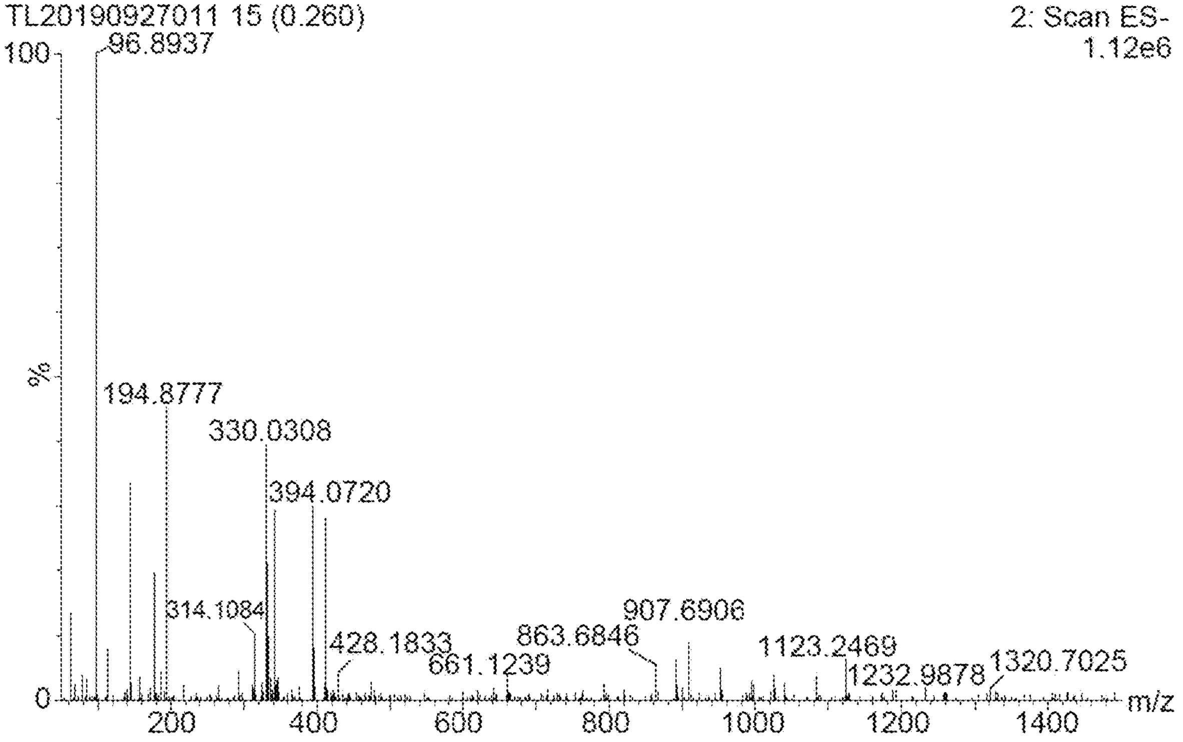
Figure 12:
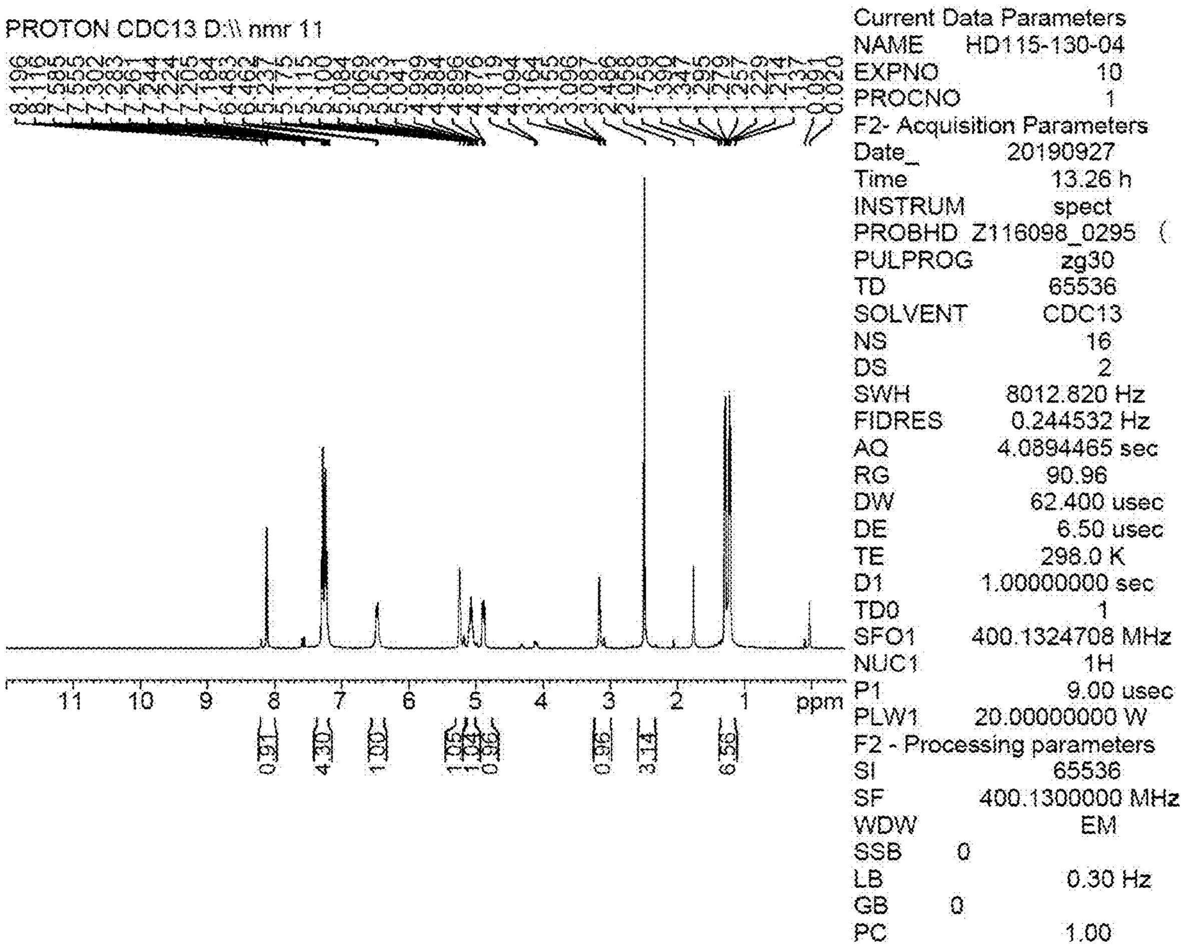
FIG. 12 is the $^1$H NMR spectrum of compound C-3 (isopropyl ester) obtained by the preparation method of the present invention.

Characterization data of compound C-3: [MS+H]: 298.4; its mass spectrum is shown in FIG. 11, and the $^1H$ NMR spectrum is shown in FIG. 12.

Synthesis of Compound D-3 (Isopropyl Ester)

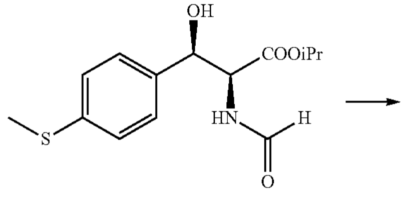

C-3

-continued

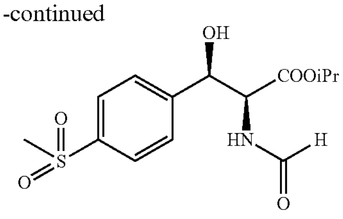

D-3

In a reactor were added sequentially 1000 g of C-3, 8 g of EDTA, 3000 g of methanol, the resulting mixture was heated to 45° C. and stirred. Nine hundred grams (900 g) of manganese dioxide was slowly added while controlling the temperature at 45° C.-55° C., and the temperature was maintained for about 1 hour. Reaction was lasted for 6-8 hours. Sampling and monitoring were conducted, and the reaction was terminated when the remaining starting material of C-3 was less than or equal to 1%. The reaction solution was transferred to a concentration reactor and concentrated under reduced pressure, the internal temperature was controlled at 40° C.-60° C., and the concentration was conducted until there was almost no methanol remaining, and the distillation was terminated. Then tap water was added to the reactor, and the temperature was lowered to 10° C.-20° C. and held for 1 hour. Crystal precipitation was conducted when the temperature was maintained. The crystals were discharged and centrifuged to give 834 g of compound D-3 in a yield of 75.3%. [MS+H]: 330.1. The chiral HPLC spectrum of compound D-3 is shown in FIG. 13.

Synthesis of Intermediate TM-3 (Isopropyl Ester) of Florfenicol

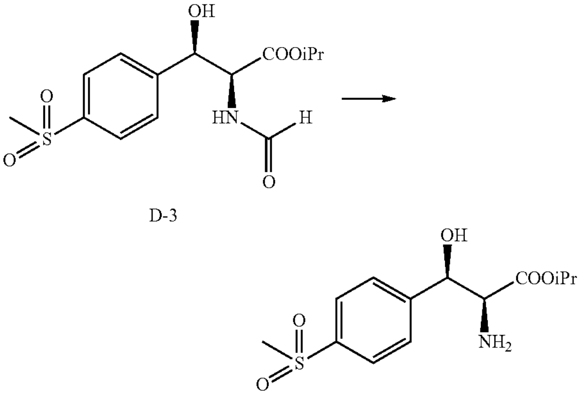

D-3

TM-3

Figure 15:
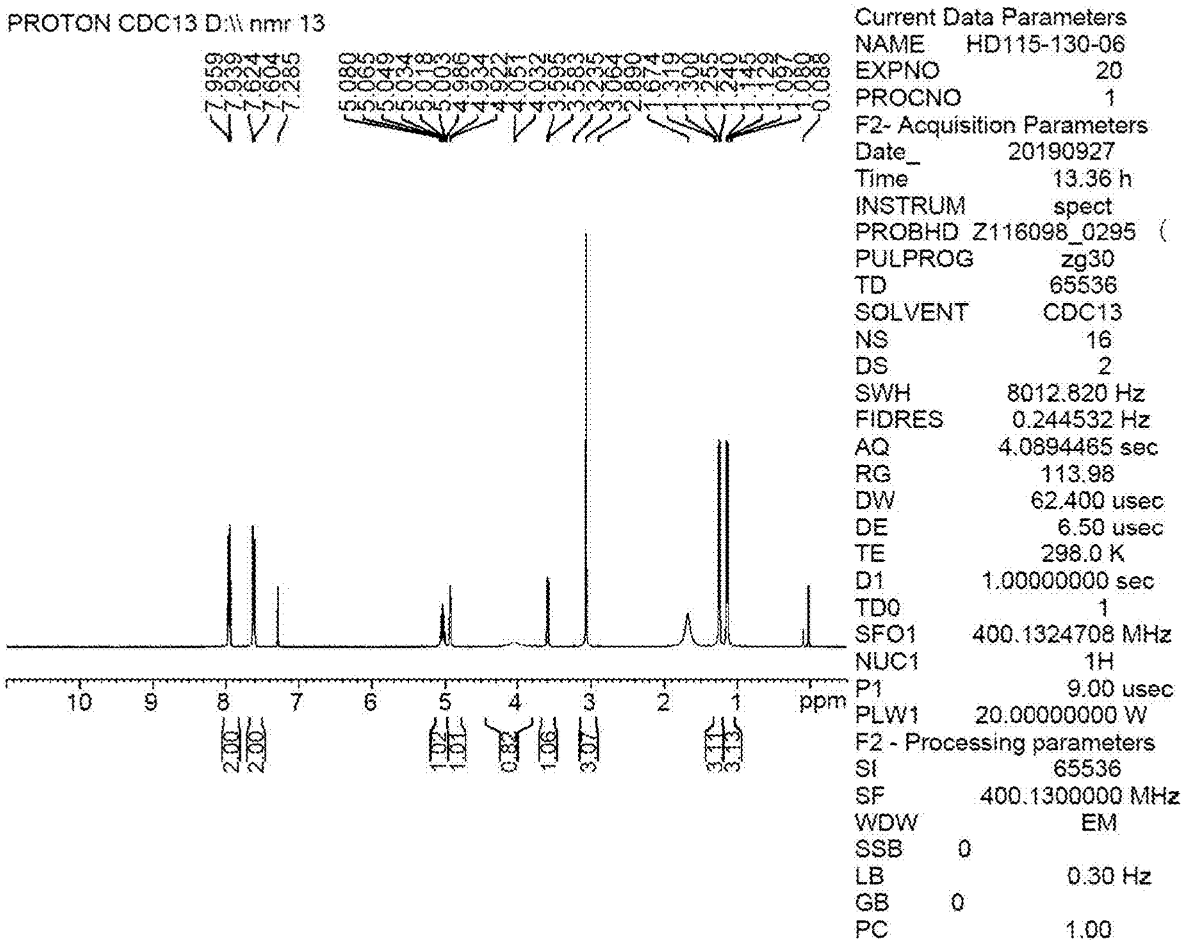
FIG. 15 is the $^1$H NMR spectrum of intermediate TM-3 (isopropyl ester) obtained by the preparation method of the present invention.

In a reactor were added sequentially 3000 g of methanol, 1000 g of D-3 and 600 g of phosphoric acid, the temperature of the resulting mixture was increased to 50° C., and the reaction was conducted for 4 hours while the temperature was maintained. Sampling and monitoring were conducted, and the reaction was terminated when the remaining starting material of D-3 was less than 1%. Concentration was initiated under reduced pressure while the internal temperature was controlled at 40° C.-60° C. Distillation was continued until there was no remaining methanol. Then water and activated carbon were added to remove insoluble substances, the filtrate was cooled to a temperature below 15° C. Ammonia was slowly added dropwise, pH was adjusted to 7.5-8, and a large amount of white solids precipitated. After adjustment of pH, the solution was cooled to 0° C.-5° C. Crystal growth was conducted for 2 hours while the temperature was maintained. The mixture was discharged into a scraper centrifuge and rotation filtering was followed. The filter cake was rinsed with water and dried to give 860 g of compound TM-3 in a yield of 94%, chiral purity: 98.7%. Characterization data of compound TM-3: [MS+H]: 302.1, the chiral HPLC spectrum is shown in FIG. 14, and its $^{1}H$ NMR spectrum is shown in FIG. 15.

Example 4

Synthesis of Compound C-4 (Tert-Butyl Ester)

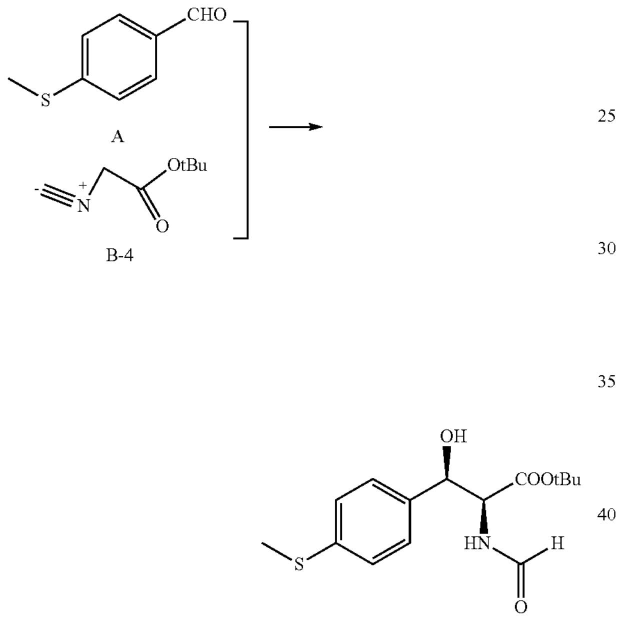

A

B-4

C-4

In a reactor were added sequentially 700 g of acetonitrile, 100 g of compound A, and 0.5 g of catalyst represented by Formula 1-1. The resulting mixture was stirred for about 10 minutes while the reaction system temperature was controlled at 15° C.-20° C. and 93 g of compound B-4 was dissolved in acetonitrile. The solution of compound B-4 in acetonitrile was slowly dripped into the reactor, with the dripping time controlled within about 0.5 hour. A slight exotherm was observed. After the dripping was completed, the reaction was continued for 1 hour. The reaction mixture was sampled and monitored for completion of the reaction, and workup was followed. To the reaction solution was added 5 wt % $H_2SO_4$ and the reaction solution was heated to 45° C. and stirred for 1 hour. And then filtration was conducted to remove insoluble matters, and the filtrate was reduced to dryness by removing the solvent under reduced pressure, giving 143 g of compound C-4 in a yield of 78.5%.

Figure 16:
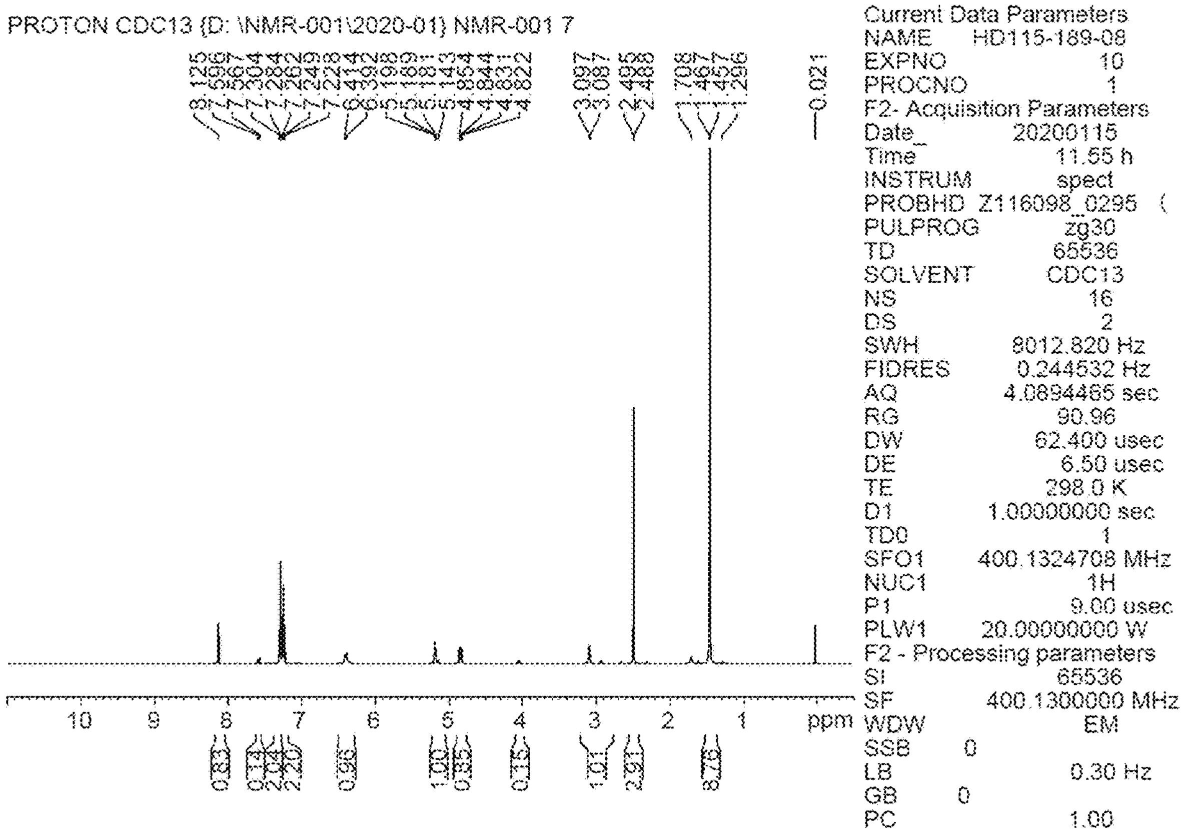
FIG. 16 is the $^1$H NMR spectrum of compound C-4 (tert-butyl ester) obtained by the preparation method of the present invention.
Figure 17:
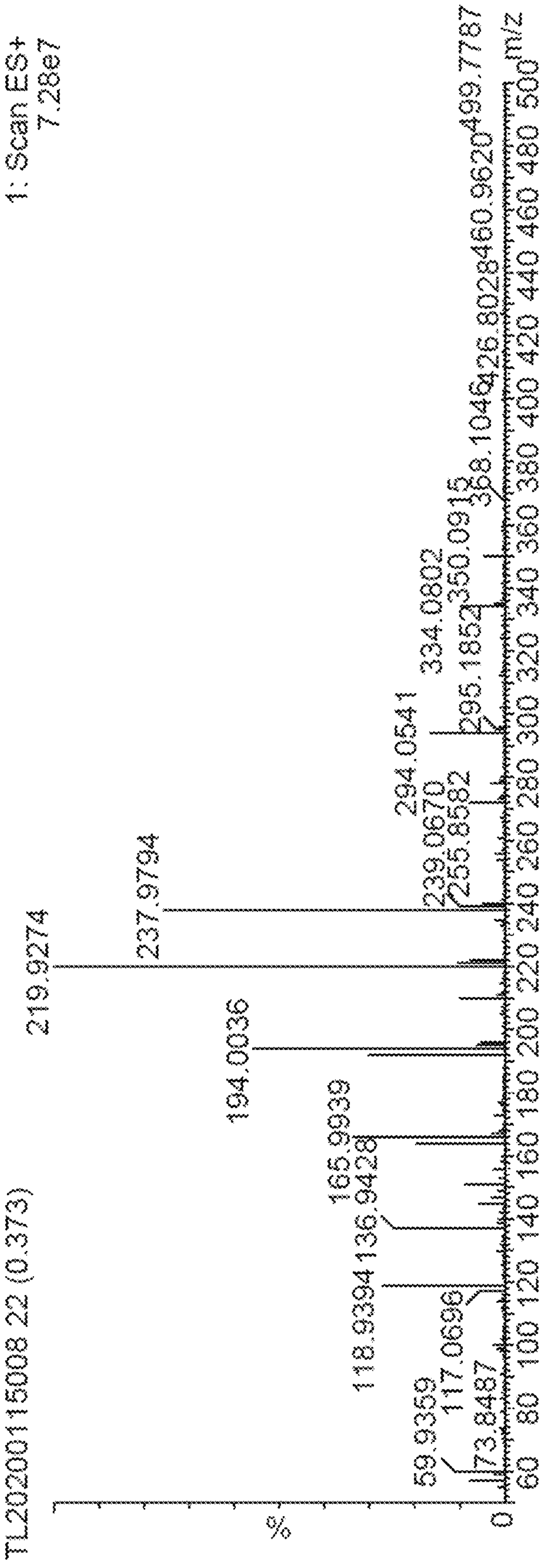
FIG. 17 is the mass spectrum of compound C-4 (tert-butyl ester) obtained by the preparation method of the present invention.
Figure 17:
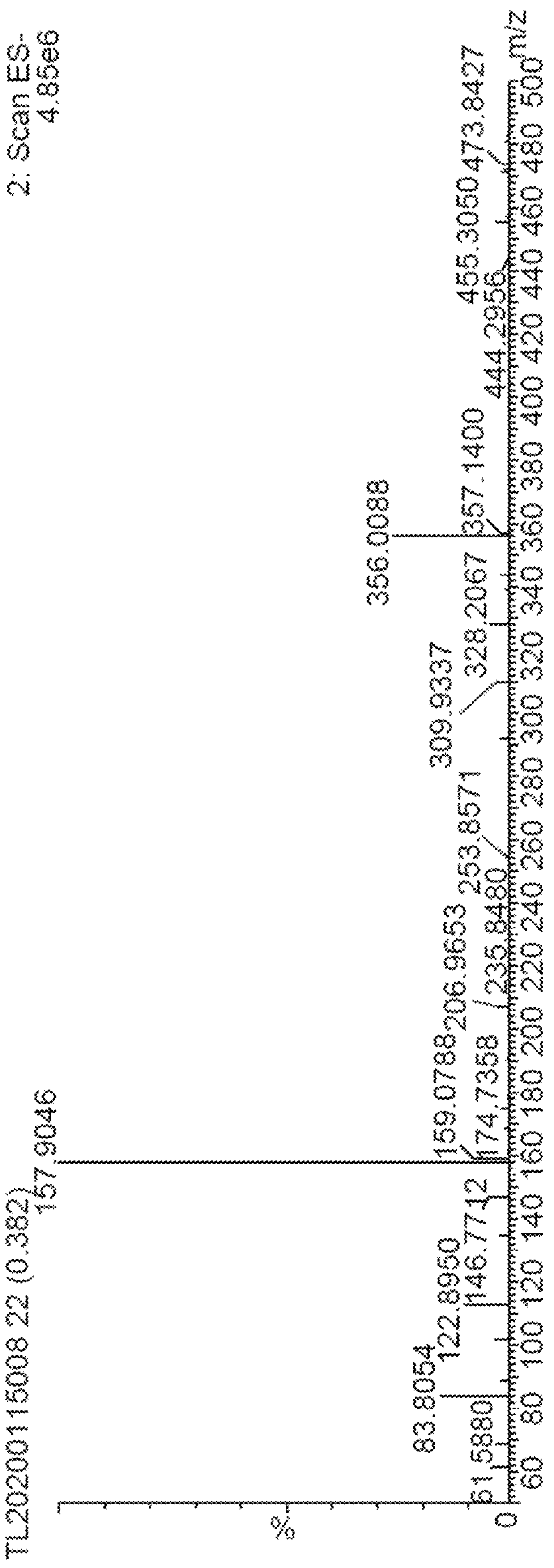

Characterization data of compound C-4: [MS+H]: 312.4, the $^{1}H$ NMR spectrum is shown in FIG. 16 and the mass spectrum is shown in FIG. 17.

Synthesis of Compound D-4 (Tert-Butyl Ester)

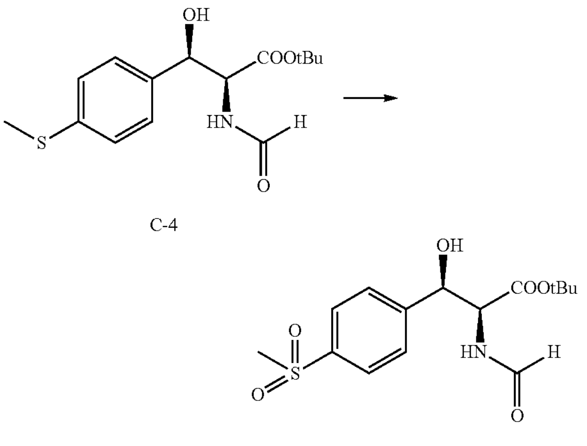

C-4

D-4

Figure 18:
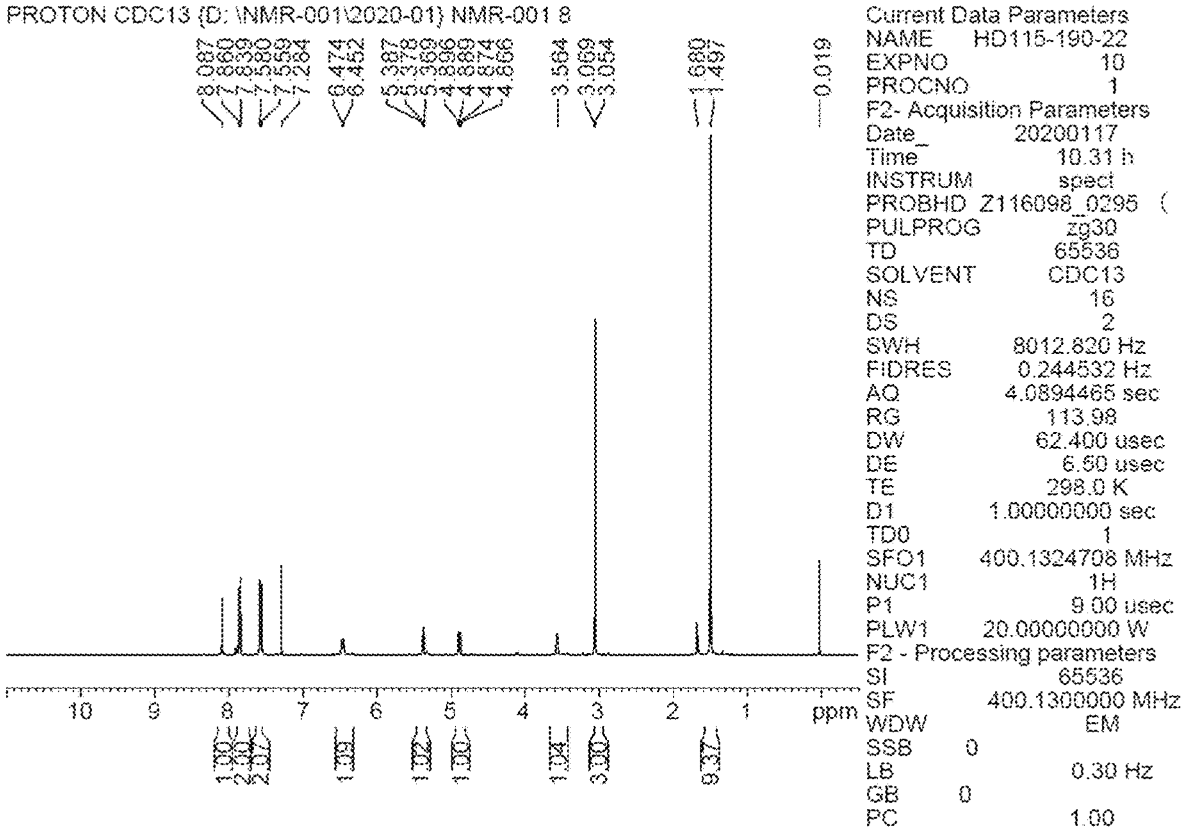
FIG. 18 is the $^1$H NMR spectrum of compound D-4 (tert-butyl ester) obtained by the preparation method of the present invention.

In a reactor were added sequentially 100 g of C-4, 0.7 g of EDTA, 300 g of methanol, the resulting mixture was heated to 45° C. and stirred. Ninety five grams (95 g) of potassium permanganate was slowly added while controlling the temperature at 45° C.-55° C., and the temperature was maintained for about 1 hour. Reaction was lasted for 6-8 hours. Sampling and monitoring were conducted, and the reaction was terminated when the remaining starting material of C-4 was less than or equal to 1%. The reaction solution was transferred to a concentration reactor and concentrated under reduced pressure, the internal temperature was controlled at 40° C.-60° C., and the concentration was conducted until there was almost no methanol remaining, and the distillation was terminated. Then tap water was added to the reactor, and the temperature was lowered to 10° C.-20° C. and held for 1 hour. Crystal precipitation was conducted when the temperature was maintained. The crystals were discharged and centrifuged to give 78 g of compound D-4. Characterization data of compound D-4: [MS+H]: 344.1; $^{1}H$ NMR spectrum is shown in FIG. 18.

Synthesis of Intermediate TM-4 (Tert-Butyl Ester) of Florfenicol

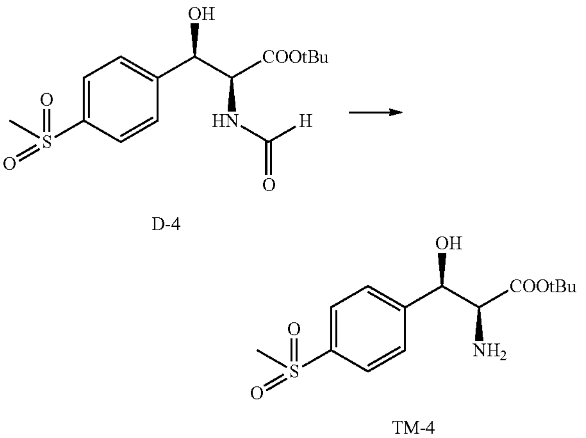

D-4

TM-4

Figure 19:
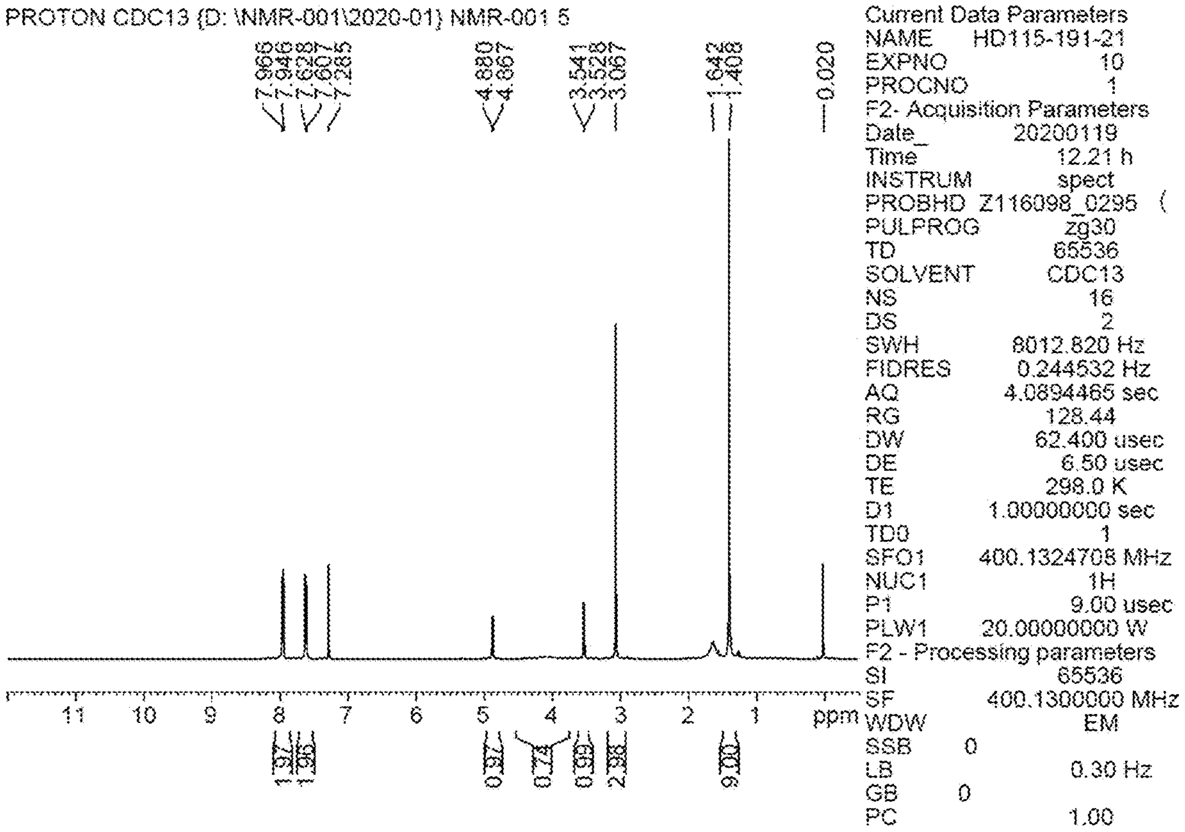
FIG. 19 is the $^1$H NMR spectrum of intermediate TM-4 (tert-butyl ester) obtained by the preparation method of the present invention.

In a reactor were added sequentially 350 g of methanol, 100 g of D-4 and 60 g of boric acid, the temperature of the resulting mixture was increased to 50° C., and the reaction was conducted for 4 hours while the temperature was maintained. Sampling and monitoring were conducted, and the reaction was terminated when the remaining starting material of compound D-4 was less than 1%. Concentration was initiated under reduced pressure while the internal temperature was controlled at 40° C.-60° C. Distillation was continued until there was no remaining methanol. Then water and activated carbon were added to remove insoluble substances, the filtrate was cooled to a temperature below 15° C. Ammonia was slowly added dropwise, pH was adjusted to 7.5-8, and a large amount of white solids precipitated. After adjustment of pH, the solution was cooled to 0° C.-5° C. Crystal growth was conducted for 2 hours while the temperature was maintained. The mixture was discharged into a scraper centrifuge and rotation filtering was followed. The filter cake was rinsed with water and dried to give 81 g of compound TM-4. Characterization data of compound TM-4: [MS+H]: 316.2; $^1$H NMR spectrum is shown in FIG. 19.

Example 5

Preparation of florfenicol from the intermediate TM (D-p-methylsulfonyl phenylserine ethyl ester) may be referred to patent publication CN101265220A, and its synthesis route is as follows.

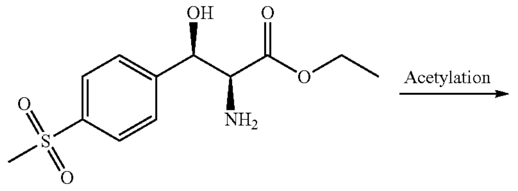

4

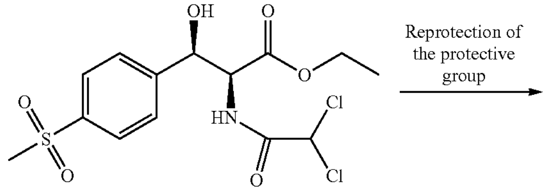

5

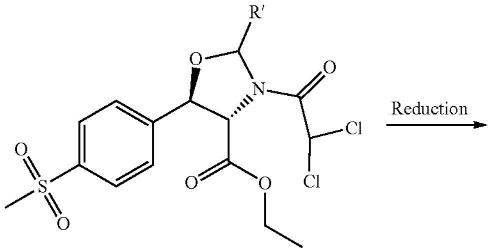

6

-continued

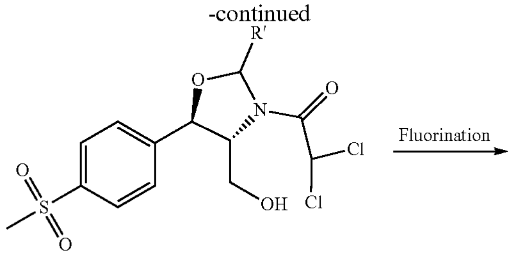

7

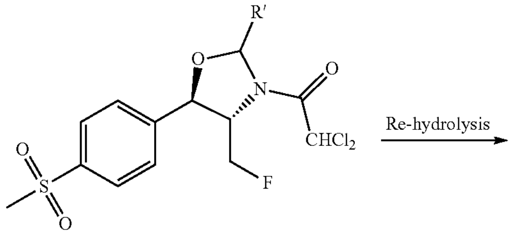

8

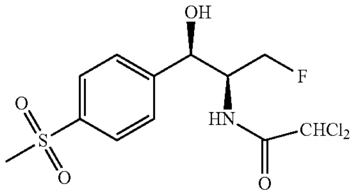

Florenicol

Protecting group R' represents one of a phthalic anhydride group, a benzonitrile group, and an allyl group.

Florfenicol is prepared from intermediates TM of florfenicol according to the process published in CN101265220A.

In a 250 ml three-necked flask were add sequentially 55 ml of methanol, 5.5 g of compound 4 (D-p-methylsulfonylphenyl serine ethyl ester, that is the intermediate TM-2 in Example 2 of the present invention), 3.0 ml of triethylamine and 11 ml of methyl dichloroacetate, and the reaction was conducted for 20 hours at 35° C., and concentration was conducted under reduced pressure so as to recover methanol. 50 ml of toluene and 50 ml of water were added to the concentrated solution, the resulting mixture was stirred for 30 minutes and filtered to give compound 5.

Compound 5 was dissolved in 60 ml of dichloromethane, and 2-methoxypropene and a catalytic amount of p-toluenesulfonic acid were added, the reaction was conducted with compound 5 and 2-methoxypropene being in a molar ratio of 1:1.5, and the reaction mixture were stirred at 40° C. for 3 hours. Then 50 ml of saturated sodium bicarbonate solution was added at room temperature and stirred for 30 minutes. Separation was followed and the aqueous phase was extracted with dichloromethane, the organic phases were combined and dried over anhydrous sodium sulfate, and the dried organic phase was concentrated to give 6.8 g of compound 6.

Reduction of Compound 6 to Prepare Compound 7

Compound 6 was dissolved in 20 ml of methanol, and 2.5 g of $KBH_4$ was dissolved in 10 ml of water. Then $KBH_4$ was added dropwise to the reaction system. The dripping speed was controlled so as to keep the temperature below 50° C. The resulting mixture was stirred for 5 hours at room temperature after the addition was complete. Filtration was conducted to obtain a crude compound 7 which can be purified by recrystallization from isopropanol, and finally 3.1 g of compound 7 is obtained.

Compound 7 is fluorinated to give compound 8, and then hydrolyzed to give the compound of florfenicol.

Figures 20, 21:
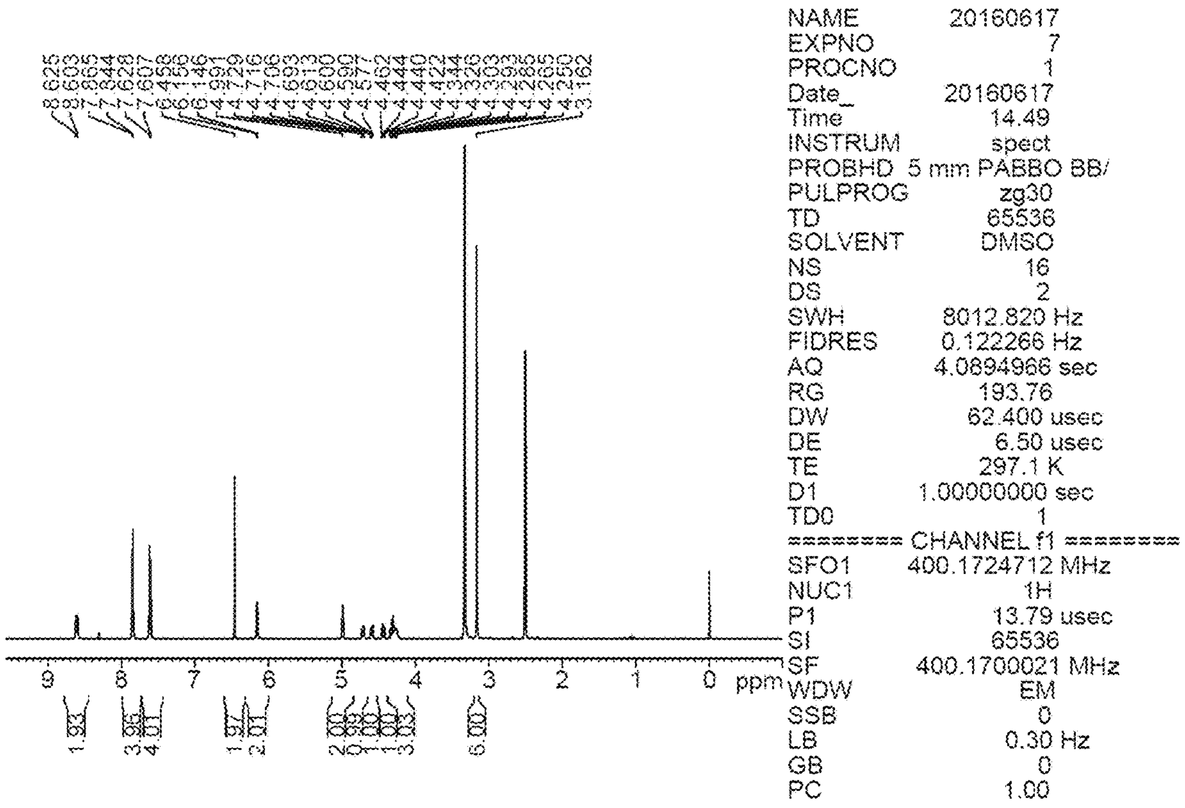
FIG. 20 is the $^1$H NMR spectrum of florfenicol prepared from the intermediate TM of the present invention.
FIG. 21 is the optical rotation detection data of florfenicol prepared from the intermediate TM of the present invention.

3.0 g of compound 7 was mixed with 30 ml of dichloromethane, stirred, and protected in a nitrogen atmosphere. 2.1 ml of Ishikawa reagent was added at room temperature, then the resulting reaction system mixture was transferred to an autoclave, and reaction was carried out at 100° C. reaction for 2 hours. Then the autoclave was cooled to room temperature. The reaction system was transferred to a 250 ml three-necked flask for re-hydrolysis. The hydrolysis process was as follows: 20 ml of hydrochloric acid having a concentration of 6 mol/L was added and heated to reflux, and refluxing was lasted for 4 hours. Then the reaction system was cooled to room temperature naturally, and 30 ml of sodium hydroxide solution having a concentration of 2 mol/L was added to adjust the pH value. The organic phase was extracted with dichloromethane (40 ml×3), and the organic phases were combined, dried over anhydrous sodium sulfate, and concentrated to give crude florfenicol. The crude florfenicol product was recrystallized from ethanol to give 0.9 g of white solid—florfenicol having a purity of 98.5%. The proton nuclear magnetic spectrum and optical rotation detection data of florfenicol are shown in FIG. 20 and FIG. 21, respectively. The optical rotation value of florfenicol obtained through (α=−18.269°), which is substantially consistent with the optical rotation value (α=−18.1°) published in CN106349130A, indicating that the preparation method of the present invention can provide the intermediate TM (D-p-methylsulfonyl phenylserine ester) of florfenicol having expected chiral configuration.

Example 6

The first step in this example is similar to the first step in Example 1, except that p-methylthio benzaldehyde was replaced with p-methylsulfonyl benzaldehyde. The specific process is as follows.

In the reactor were added sequentially 4 ml of dichloromethane, 18 mg of (0.18 mmol, 0.1 eq) triethylamine, 326 mg (1.77 mmol, 1.0 eq) of p-methylsulfonyl benzaldehyde, $Ag_2O$, and 60 mg (0.09 mmol, 0.05 eq) of catalyst represented by Formula 1-1, and the resulting mixture was stirred for about 2 min. A solution of 200 mg (1.77 mmol, 1.0 eq) of ethyl isocyanoacetate in dichloromethane was slowly added dropwise to the reaction vessel at room temperature, and solids were quickly generated in the reaction system, which made it difficult for the reaction to proceed. Complex reaction products were observed through thin layer chromatography (TLC) detection and the reaction was not ideally conducted. It can be seen from this example that in the first step of reaction, under the catalysis of the catalyst of Formula 1-1, the attempt to react p-methylsulfonyl benzaldehyde with isocyanoacetate (compound B) in order to form a chiral compound (compound C) was not successful.

In the preparation method of the intermediate TM of florfenicol claimed in the present invention, p-methylthiobenzaldehyde is reacted with isocyanoacetate under the catalysis of a chiral catalyst, and the product resulted from chiral catalysis is oxidized to give a methyl sulfone-substituted product, and the formyl group in the methyl sulfone-substituted product is removed to give an intermediate of florfenicol. In the preparation method of the present invention, the chiral center of the intermediate is directly generated through the first step reaction, and the yield of the first step product reaches 75%-80%, which is significantly higher than the yield obtained by conventional chiral resolution method. And the chiral purity is also high. The method of the present invention does not use anhydrous copper sulfate that pollutes the environment, which reduces the environmental pressure. The preparation method of the invention has good prospects for industrial application.

What is claimed is:

1. A method for preparing formula (TM), an intermediate of florfenicol, comprising the following synthetic route:

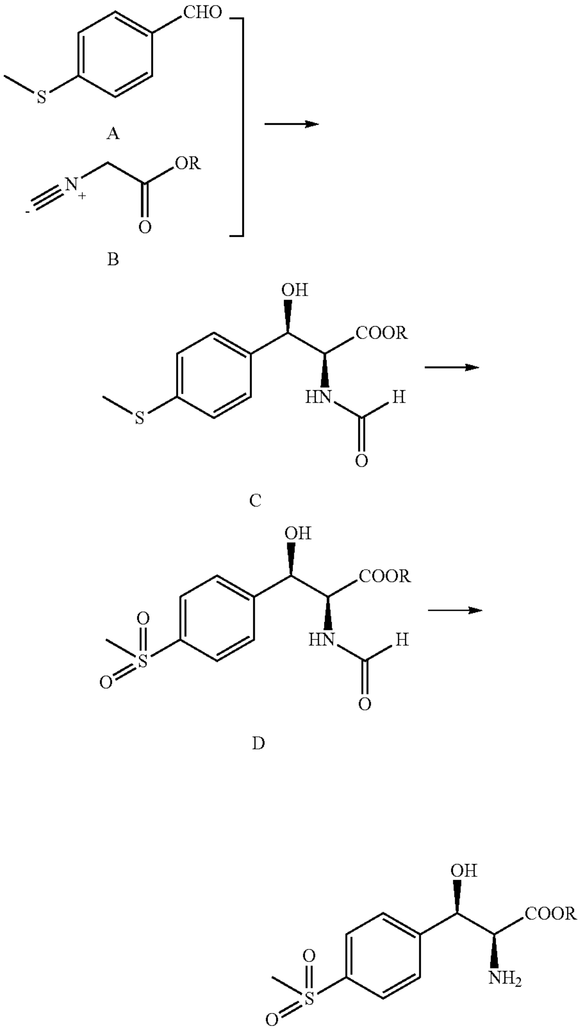

A

B

C

D

TM

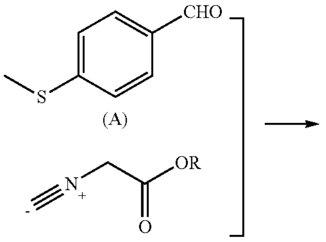

(A)

(B)

-continued

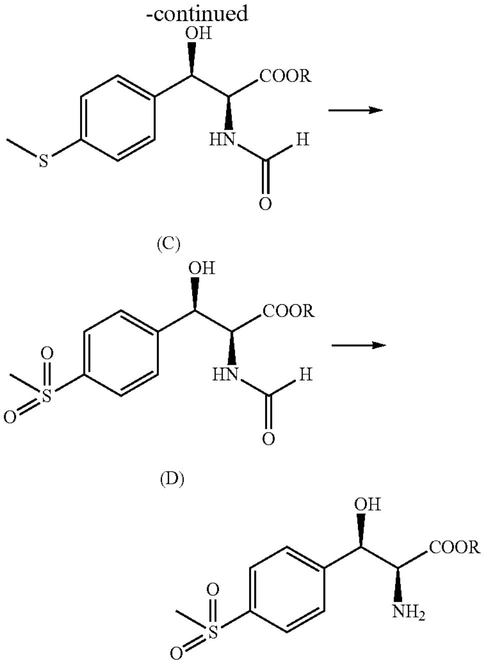

(C)

(D)

(TM)

wherein R is selected from methyl, ethyl, propyl, isopropyl, butyl, isobutyl, or tert-butyl;

and the method comprises steps of:

(1) dissolving compound (A) and compound (B) in a first organic solvent, adding a catalyst to proceed a catalysis reaction; adding a first acid after the catalysis reaction is ended; filtering out precipitated solids, and concentrating the filtrate under reduced pressure to give compound (C);

(2) oxidizing compound (C) to compound (D) by using an oxidant;

(3) removing the formyl group in compound (D) to give the intermediate (TM) of florfenicol;

wherein in step (1), the catalyst has a structure represented by Formula (1):

Formula (1)

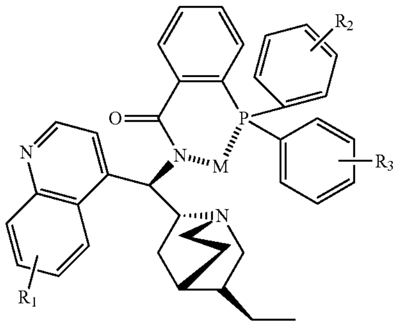

wherein M is selected from Au, Ag, or Cu;

$R_1$ is selected from methoxy, chlorine atom, or is absent;

$R_2$ is selected from methyl, phenyl, or is absent;

$R_3$ is selected from methyl, phenyl, or is absent.

2. The method according to claim 1, wherein in step (1), the molar ratio of compound (A) to compound (B) is 1:1.

3. The method according to claim 1, wherein in step (1), the catalyst is added in amount of 0.1%-0.5 wt % with respect to compound (A).

4. The method according to claim 1, wherein in step (1), the first organic solvent is selected from one or more of tetrahydrofuran, dichloromethane, tert-butanol, ethyl acetate, acetonitrile, 1,4-dioxane and methyl tert-butyl ether.

5. The method according to claim 1, wherein in step (2), compound (C) is oxidized to compound (D) by the following process: dissolving compound (C) in a second organic solvent, adding EDTA and the oxidant, reaction is conducted by controlling the reaction temperature within a range of from 40° C. to 60° C. to give compound (D).

6. The method according to claim 1, wherein in step (3), the formyl group in compound (D) is removed by the following process: dissolving compound (D) in a third organic solvent, adding a second acid to react, and after the reaction is ended, adding an alkali to adjust pH value until white solids are precipitated, thus obtaining the intermediate (TM) of florfenicol.

7. The method according to claim 4, wherein in step (1), the first acid is selected from one or more of hydrochloric acid, phosphoric acid, boric acid, carbonic acid, sulfuric acid, and nitric acid.

8. The method according to claim 5, wherein in step (2), the second organic solvent is selected from one or more of methanol, ethanol, glycerol, and isopropanol.

9. The method according to claim 5, wherein in step (2), the oxidant is selected from one or more of potassium permanganate, $MnO_2$, m-chloroperoxybenzoic acid, and hydrogen peroxide.

10. The method according to claim 5, wherein in step (2), the oxidant is hydrogen peroxide, and the mass ratio of compound (C), hydrogen peroxide to EDTA is 1:0.85-1.0:0.005-0.01.

11. The method according to claim 6, wherein in step (3), the third organic solvent is selected from one or more of methanol, ethanol, glycerol, and isopropanol.

12. The method according to claim 6, wherein in step (3), the mass ratio of compound (D) to the second acid is 1:0.4-0.8.

13. The method according to claim 6, wherein in step (3), the second acid is selected from one or more of hydrochloric acid, phosphoric acid, boric acid, carbonic acid, sulfuric acid, and nitric acid.

14. The method according to claim 6, wherein in step (3), the alkali is selected from one or more of sodium hydroxide, potassium hydroxide, potassium carbonate, sodium carbonate, sodium bicarbonate, and ammonia.

* * * * *